United States Patent [19]

Banno et al.

[11] Patent Number: 4,482,560

[45] Date of Patent: Nov. 13, 1984

[54] CARBOSTYRIL DERIVATIVES, AND ANTIHISTAMINIC AGENTS CONTAINING THE SAME

[75] Inventors: Kazuo Banno; Takafumi Fujioka; Yasuo Oshiro; Kazuyuki Nakagawa, all of Tokushima, Japan

[73] Assignee: Otsuka Pharmaceutical Co., Ltd., Tokyo, Japan

[21] Appl. No.: 357,769

[22] Filed: Mar. 12, 1982

Related U.S. Application Data

[63] Continuation-in-part of Ser. No. 327,460, Dec. 4, 1981, abandoned, which is a continuation of Ser. No. 186,340, Sep. 11, 1980, abandoned.

[30] Foreign Application Priority Data

Sep. 18, 1979 [JP] Japan .............................. 54-120452
Sep. 28, 1979 [JP] Japan .............................. 54-125565

[51] Int. Cl.³ ................... A61K 31/47; C07D 215/22; C07D 215/26
[52] U.S. Cl. ................................. 424/258; 546/157; 546/158
[58] Field of Search ................. 546/157, 158; 424/258

[56] References Cited

U.S. PATENT DOCUMENTS

| | | | |
|---|---|---|---|
| 3,629,266 | 12/1971 | Havera | 546/158 |
| 3,910,924 | 10/1975 | Tamura et al. | 546/158 |
| 3,994,900 | 11/1976 | Krapcho et al. | 546/158 X |
| 4,147,869 | 4/1979 | Nakagawa et al. | 546/158 |
| 4,210,753 | 7/1980 | Tominaga et al. | 544/128 |
| 4,256,890 | 3/1981 | Nakagawa et al. | 546/158 |
| 4,330,549 | 5/1982 | Friebe et al. | 424/267 |

FOREIGN PATENT DOCUMENTS

| | | | |
|---|---|---|---|
| 2912105 | 10/1979 | Fed. Rep. of Germany . | |
| 0106977 | 8/1975 | Japan . | |
| 0142576 | 11/1975 | Japan . | |
| 113979 | 9/1977 | Japan . | |
| 0136177 | 11/1977 | Japan . | |
| 0108978 | 9/1978 | Japan | 546/158 |
| 0016478 | 2/1979 | Japan . | |
| 0002693 | 1/1980 | Japan . | |
| 0089221 | 7/1980 | Japan . | |
| 0089222 | 7/1980 | Japan . | |

Primary Examiner—Paul M. Coughlan, Jr.
Assistant Examiner—Diana G. Rivers
Attorney, Agent, or Firm—Finnegan, Henderson, Farabow, Garrett & Dunner

[57] ABSTRACT

Novel carbostyril derivatives and their salts having antihistaminic effects and are useful as antihistaminic agents, represented by the general formula (1),

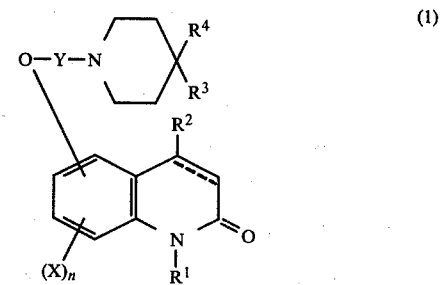

wherein $R^1$ is a hydrogen atom, a lower alkenyl group, a lower alkynyl group or a lower alkyl group which may have phenyl group(s) as the substituted group(s); $R^2$ is a hydrogen atom, a lower alkyl group or a phenyl group; $R^3$ is a lower alkyl group having phenyl group(s) as the substituted group(s), or a phenyl group which may have 1 to 3 substituted groups selected from the group consisting of halogen atoms, lower alkyl groups and lower alkoxy groups; $R^4$ is a hydrogen atom, a hydroxyl group or a lower alkanoyl group; X is a halogen atom; Y is a lower alkylene group which may have hydroxyl group(s) as the substituent(s); n is 0, 1 or 2; the carbon-carbon bond between 3- and 4-positions in the carbostyril skeleton is a single or double bond; provided that when $R^3$ is a lower alkyl group having phenyl group(s) as the substituted group(s), then $R^4$ should be neither a hydroxyl group nor a lower alkanoyl group.

24 Claims, No Drawings

CARBOSTYRIL DERIVATIVES, AND ANTIHISTAMINIC AGENTS CONTAINING THE SAME

CROSS-REFERENCE TO RELATED APPLICATION

This application is a continuation-in-part of application Ser. No. 327,460 filed on Dec. 4, 1981 which is in turn a continuation application of U.S. Ser. No. 186,340 filed on Sept. 11, 1980 both now abandoned.

The present invention relates to novel carbostyril derivatives, their salts, process for producing the same and antihistaminic composition containing said carbostyril derivative(s) as the active ingredient(s).

Carbostyril derivatives and their salts of the present invention are represented by the general formula (1) as follows:

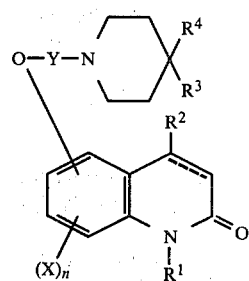

(1)

wherein $R^1$ is a hydrogen atom, a lower alkenyl group, a lower alkynyl group or a lower alkyl group which may have phenyl group(s) as the substituted group(s); $R^2$ is a hydrogen atom, a lower alkyl group or a phenyl group; $R^3$ is a lower alkyl group having phenyl group(s) as the substituted group(s), or a phenyl group which may have 1 to 3 substituted groups selected from the group consisting of halogen atoms, lower alkyl groups and lower alkoxy groups; $R^4$ is a hydrogen atom, a hydroxyl group or a lower alkanoyl group; X is a halogen atom; Y is a lower alkylene group which may have hydroxyl group(s) as the substituent(s); n is 0, 1 or 2; the carbon-carbon bond between 3- and 4-positions in the carbostyril skeleton is a single or double bond; provided that when $R^3$ is a lower alkyl group having phenyl group(s) as the substituted group(s) then $R^4$ should be neither a hydroxyl group nor a lower alkanoyl group.

The carbostyril derivatives and their salts represented by the general formula (1) of the present invention have excellent antihistaminic and local anesthesia effects and are useful for antihistaminic agents and local anesthetic agent.

The present invention provides antihistaminic agents containing at least one carbostyril derivative or salt thereof mentioned above as the active ingredient.

As the results known from an extensive animal tests, the carbostyril derivatives of the present invention have excellent antihistaminic effects with less side-effects such as central nervous controlling effect or β-adrenergic nerve blocking effect.

There are described in various articles of medical and pharmaceutical publications, for example, Goodman-Gilman's "YAKURI SHO" (Textbook of Pharmacology) (the first-volume)-"YAKUBUTSU CHIRYO NO KISO TO RINSHO" (Fundamental and Clinic of Pharmacotherapy), pages 781–835 (published from Hirokawa Shoten Co., (1974)); "SHIN-OYO YAKURIGAKU" (New Applied Pharmacology) by Hisashi Uno, pages 307 to 319 (published from Nagai Shoten Co., (1970)); "SHIN-YAKU TO RINSHO" (Journal of New Remedies & Clinic), Vol. 20, No. 11, pages 129–133 (1971); and "KISO TO RINSHO" (Laboratory and Clinic), Vol. 10, No. 10, pages 17–27 (1976), that generally an antihistaminic agent does not inhibit the isolation of a combined type histamine formed by the antigen-antibody reaction in allergies, but inhibits the combination (a competitive antagonism) of an active type histamine with a histamine-acceptor to show antihistaminic effect. The antihistaminic agents of the present invention are, therefore, effective as treating agents and prophylactic agents for various allergic diseases and symptoms caused by the combination of histamine and histamine-acceptor, for example allergic symptoms in respiratory tract, such as sneezing, snuffles, prickling at eyes, nose and throat, hay fever, pollinosis, acute uriticaria (itching, edema, flare and the like), vascular edema, pruritus, atopic dermatitis, insect bite, contact-type dermatitis such as "urushi kabure" (ivy poisoning), urticaria and edemic disorder in serum disease, allergic rhinitis, allergic conjunctivitis or corneitis. Furthermore, the antihistaminic agents of the present invention can also be used as supplemental agents for curing systemic anaphylaxis in which autacoids other than histamine may perform as important role. Additionally the carbostyril derivatives of the present invention can also be used as diagnostic reagents for measuring the activity of excretion of gastric juice, especially the activity of gastric acidity.

Some carbostyril derivatives having useful pharmacological effects, such as antiinflammatory effect, inhibitory effect on blood platelet aggregation, central nervous system controlling effect and β-adrenergic nerve blocking effect are known in prior art literatures, for example U.S. Pat. Nos. 3,994,900, 4,147,869; DOS Nos. 2302027, 2711719; Japanese Patent Application Kokai (Laid-open) Nos. 106977/1975, 142576/1975. However, these prior art literatures do not disclose that these carbostyril derivatives have antihistaminic effects.

On the other hand, other carbostyril derivatives having antihistaminic effects are known in other prior art literatures, for example, DOS No. 2912105, Japanese Patent Application Kokai (Laid-open) Nos. 16478/1979, 2693/1980, 89221/1980, 89222/1980. However, these carbostyril derivatives having antihistaminic effects known in the art are different from the carbostyril derivatives of the present invention with respect to the type and the substituted positions of the substituted groups.

Additionally, the carbostyril derivatives of the present invention have antihistaminic effects selectively, but have less properties of central nervous system controlling effects and β-adrenergic nerve blocking effects as compared with the carbostyril derivatives known in the prior art literatures.

In the general formula (1), the specific examples of the groups defined in the respective symbols of $R^1$, $R^2$, $R^3$, $R^4$, X and Y are shown below.

The term "a lower alkenyl group" means a straight or branched chain alkenyl group having 2 to 6 carbon atoms, such as a vinyl group, allyl group, 2-butenyl group, 1-methyl-2-butenyl group, 2-pentenyl group, 2-hexenyl group and the like.

The term "a lower alkynyl group" means a straight or branched chain alkynyl group having 2 to 6 carbon atoms, such as an ethynyl group, propargyl group, 2-butynyl group, 1-methyl-2-propargyl group, 2-pentynyl group, 2-hexynyl group and the like.

The term "a lower alkyl group which may have phenyl group(s) as the substituted group(s)" means a straight or branched chain alkyl group having 1 to 6 carbon atoms which may have phenyl group(s) as the substituted group(s), such as an methyl group, ethyl group, propyl group, isopropyl group, butyl group, tert-butyl group, pentyl group, hexyl group, benzyl group, 1-phenylethyl group, 2-phenylethyl group, 3-phenylpropyl group, 4-phenylbutyl group, 1,1-dimethyl-2-phenylethyl group, 5-phenylpentyl group, 6-phenylhexyl group, diphenylmethyl group and the like.

The term "a lower alkyl group" means a straight or branched chain alkyl group having 1 to 6 carbon atoms, such as a methyl group, ethyl group, propyl group, isopropyl group, butyl group, tert-butyl group, pentyl group, hexyl group and the like.

The term "a lower alkyl group having phenyl group(s) as the substituted group(s) means a straight or branched chain alkyl group having 1 to 6 carbon atoms, and having phenyl group(s) as the substituted group(s), such as a benzyl group, 1-phenylethyl group, 2-phenylethyl group, 3-phenylpropyl group, 4-phenylbutyl group, 1,1-dimethyl-2-phenylethyl group, 5-phenylpentyl group, 6-phenylhexyl group, diphenylmethyl group and the like.

The term "a halogen atom" means a fluorine atom, a chlorine atom, a bromine atom and iodine atom.

The term "a lower alkoxy group" means a straight or branched chain alkoxy group having 1 to 6 carbon atoms, such as a methoxy group, ethoxy group, propoxy group, isopropoxy group, butoxy group, tert-butoxy group, pentyloxy group, hexyloxy group and the like.

The term "a lower alkanoyl group" means a straight or branched chain alkanoyl group having 1 to 6 carbon atoms, such as a formyl group, acetyl group, propionyl group, butyryl group, isobutyryl group, pentanoyl group, tert-butylcarbonyl group, hexanoyl group and the like.

The term "a lower alkylene group which may have hydroxyl group(s) as the substituted group(s)" means a straight or branched chain alkylene group having 1 to 6 carbon atoms which may have hydroxyl group(s) as the substituted group(s), such as a methylene group, ethylene group, trimethylene group, 2-methyltrimethylene group, 1-methyltrimethylene group, tetramethylene group, pentamethylene group, hexamethylene group, 2-ethylethylene group, 2,2-dimethyltrimethylene group, 2-hydroxytrimethylene group, 2-hydroxytetramethylene group, 2,3-dihydroxytetramethylene group, 3-hydroxypentamethylene group and the like.

Typical compounds included in the carbostyril derivatives represented by the general formula (1) are exemplified as follows. The meaning of "3,4-dehydro compound" as mentioned at the end of the name of each compounds is that a compound having a double bond between 3- and 4-positions in the carbostyril skeleton.

5-[2-Hydroxy-3-(4-phenyl-1-piperidyl)propoxy]-3,4-dihydrocarbostyril and its 3,4-dehydro compound 6-[2-Hydroxy-3-(4-phenyl-1-piperidyl)propoxy]-3,4-dihydrocarbostyril and its 3,4-dehydro compound 7-[2-Hydroxy-3-(4-phenyl-1-piperidyl)propoxy]-3,4-dihydrocarbostyril and its 3,4-dehydro compound 1-Methyl-5-[2-hydroxy-3-(4-phenyl-1-piperidyl)-propoxy]-3,4-dihydrocarbostyril and its 3,4-dehydro compound 1-Methyl-7-[2-hydroxy-3-(4-phenyl-1-piperidyl)-propoxy]-3,4-dihydrocarbostyril and its 3,4-dehydro compound 1-Methyl-8-[2-hydroxy-3-(4-phenyl-1-piperidyl)-propoxy]-3,4-dihydrocarbostyril and its 3,4-dehydro compound 1-Allyl-5-[2-hydroxy-3-(4-phenyl-1-piperidyl)propoxy]-3,4-dihydrocarbostyril and its 3,4-dehydro compound 1-Allyl-7-[2-hydroxy-3-(4-phenyl-1-piperidyl)propoxy]-3,4-dihydrocarbostyril and its 3,4-dehydro compound 1-Benzyl-5-[2-hydroxy-3-(4-phenyl-1-piperidyl)propoxy]-3,4-dihydrocarbostyril and its 3,4-dehydro compound 1-(4-Phenylbutyl)-6-[2-hydroxy-3-(4-phenyl-1-piperidyl)propoxy]-3,4-dihydrocarbostyril and its 3,4-dehydro compound 1-Benzyl-7-[2-hydroxy-3-(4-phenyl-1-piperidyl)propoxy]-3,4-dihydrocarbostyril and its 3,4-dehydro compound 1-Propargyl-5-[2-hydroxy-3-(4-phenyl-1-piperidyl)-propoxy]-3,4-dihydrocarbostyril and its 3,4-dehydro compound 1-Propargyl-7-[2-hydroxy-3-(4-phenyl-1-piperidyl)-propoxy]-3,4-dihydrocarbostyril and its 3,4-dehydro compound 6-Chloro-5-[2-hydroxy-3-(4-phenyl-1-piperidyl)propoxy]-3,4-dihydrocarbostyril and its 3,4-dehydro compound 1-Methyl-5-bromo-6-[2-hydroxy-3-(4-phenyl-1-piperidyl)propoxy]-3,4-dihydrocarbostyril and its 3,4-dehydro compound 6-Fluoro-7-[2-hydroxy-3-(4-phenyl-1-piperidyl)propoxy]-3,4-dihydrocarbostyril and 3,4-dehydro compound 1-Benzyl-5-chloro-8-[2-hydroxy-3-(4-phenyl-1-piperidyl)propoxy]-3,4-dihydrocarbostyril and its 3,4-dehydro compound 6,8-Dichloro-5-[2-hydroxy-3-(4-phenyl-1-piperidyl)-propoxy]-3,4-dihydrocarbostyril and its 3,4-dehydro compound 6-Chloro-8-bromo-7-[2-hydroxy-3-(4-phenyl-1-piperidyl)propoxy]-3,4-dihydrocarbostyril and its 3,4-dehydro compound 1-Methyl-5,6-dibromo-8-[2-hydroxy-3-(4-phenyl-1-piperidyl)propoxy]-3,4-dihydrocarbostyril and its 3,4-dehydro compound 6-[2-Hydroxy-3-(4-benzyl-1-piperidyl)propoxy]-3,4-dihydrocarbostyril and its 3,4-dehydro compound 7-[2-Hydroxy-3-(4-benzyl-1-piperidyl)propoxy]-3,4-dihydrocarbostyril and its 3,4-dehydro compound 5-[2-Hydroxy-3-(4-benzyl-1-piperidyl)propoxy]-3,4-dihydrocarbostyril and its 3,4-dehydro compound 1-Benzyl-5-[2-hydroxy-3-(4-benzyl-1-piperidyl)propoxy]-3,4-dihydrocarbostyril and its 3,4-dehydro compound 8-[2-Hydroxy-3-(4-benzyl-1-piperidyl)propoxy]-3,4-dihydrocarbostyril and its 3,4-dehydro compound 1-Methyl-5-[2-hydroxy-3-(4-benzyl-1-piperidyl)propoxy]-3,4-dihydrocarbostyril and its 3,4-dehydro compound 1-Methyl-7-[2-hydroxy-3-(4-benzyl-1-piperidyl)propoxy]-3,4-dihydrocarbostyril and its 3,4-dehydro compound 1-Propargyl-7-[2-hydroxy-3-(4-benzylpiperidyl)-propoxy]-3,4-dihydrocarbostyril and its 3,4-dehydro compound 1-Allyl-5-[2-hydroxy-3-(4-benzyl-1-piperidyl)propoxy]-3,4-dihydrocarbostyril and its 3,4-dehydro compound 8-Bromo-5-[2-hydroxy-3-(4-benzyl-1-piperidyl)propoxy]-3,4-dihydrocarbostyril and its 3,4-dehydro compound
1-Methyl-6-chloro-7-[2-hydroxy-3-(4-benzyl-1-piperidyl)propoxy]-3,4-dihydrocarbostyril and its 3,4-dehydro compound
1-Benzyl-6,8-dichloro-5-[2-hydroxy-3-(4-benzyl-1-piperidyl)propoxy]-3,4-dihydrocarbostyril and its 3,4-dehydro compound
1-Allyl-6-chloro-7-[2-hydroxy-3-(4-benzyl-1-piperidyl)propoxy]-3,4-dihydrocarbostyril and its 3,4-dehydro compound
6,8-Dibromo-5-[2-hydroxy-3-(4-benzyl-1-piperidyl)propoxy]-3,4-dihydrocarbostyril and its 3,4-dehydro compound
5-{2-Hydroxy-3-[4-(2-phenylethyl)-1-piperidyl]propoxy}-3,4-dihydrocarbostyril and its 3,4-dehydro compound
1-Methyl-7-{2-hydroxy-3-[4-(1-phenylethyl)-1-piperidyl]propoxy}-3,4-dihydrocarbostyril and its 3,4-dehydro compound
1-Benzyl-5-{2-hydroxy-3-[4-(4-phenylbutyl)-1-piperidyl]propoxy}-3,4-dihydrocarbostyril and its 3,4-dehydro compound
5-(4-Benzyl-1-piperidylmethoxy)-3,4-dihydrocarbostyril and 3,4-dehydro compound
5-[2-(4-Benzyl-1-piperidyl)ethoxy]-3,4-dihydrocarbostyril and its 3,4-dehydro compound
7-[2-(4-Benzyl-1-piperidyl)ethoxy]-3,4-dihydrocarbostyril and its 3,4-dehydro compound
5-[3-(4-Benzyl-1-piperidyl)propoxy]-3,4-dihydrocarbostyril and its 3,4-dehydro compound
6-[3-(4-Benzyl-1-piperidyl)propoxy]-3,4-dihydrocarbostyril and its 3,4-dehydro compound
7-[3-(4-Benzyl-1-piperidyl)propoxy]-3,4-dihydrocarbostyril and its 3,4-dehydro compound
8-[3-(4-Benzyl-1-piperidyl)propoxy]-3,4-dihydrocarbostyril and its 3,4-dehydro compound
5-[4-(4-Benzyl-1-piperidyl)butoxy]-3,4-dihydrocarbostyril and its 3,4-dehydro compound
7-[5-(4-Benzyl-1-piperidyl)pentyloxy]-3,4-dihydrocarbostyril and its 3,4-dehydro compound
7-[6-(4-Benzyl-1-piperidyl)hexyloxy]-3,4-dihydrocarbostyril and its 3,4-dehydro compound
1-Methyl-5-[3-(4-benzyl-1-piperidyl)propoxy]-3,4-dihydrocarbostyril and its 3,4-dehydro compound
1-Methyl-7-[3-(4-benzyl-1-piperidyl)propoxy]-3,4-dihydrocarbostyril and its 3,4-dehydro compound
1-Hexyl-7-[3-(4-benzyl-1-piperidyl)propoxy]-3,4-dihydrocarbostyril and its 3,4-dehydro compound
1-Allyl-5-[3-(4-benzyl-1-piperidyl)propoxy]-3,4-dihydrocarbostyril and its 3,4-dehydro compound
1-Allyl-7-[3-(4-benzyl-1-piperidyl)propoxy]-3,4-dihydrocarbostyril and its 3,4-dehydro compound
1-(1-Methylallyl)-7-[3-(4-benzyl-1-piperidyl)propoxy]-3,4-dihydrocarbostyril and its 3,4-dehydro compound
1-Propargyl-7-[3-(4-benzyl-1-piperidyl)propoxy]-3,4-dihydrocarbostyril and its 3,4-dehydro compound
1-Propargyl-5-[3-(4-benzyl-1-piperidyl)propoxy]-3,4-dihydrocarbostyril and its 3,4-dehydro compound
1-Benzyl-5-[3-(4-benzyl-1-piperidyl)propoxy]-B 3,4-dihydrocarbostyril and its 3,4-dehydro compound
1-(4-Phenylbutyl)-7-[3-(4-benzyl-1-piperidyl)propoxy]-3,4-dihydrocarbostyril and its 3,4-dehydro compound
1-Benzyl-7-[3-(4-benzyl-1-piperidyl)propoxy]-3,4-dihydrocarbostyril and its 3,4-dehydro compound
5-{3-[4-(2-Phenylethyl)-1-piperidyl]propoxy}-3,4-dihydrocarbostyril and its 3,4-dehydro compound
7-{3-[4-(2-Phenylethyl)-1-piperidyl]propoxy}-3,4-dihydrocarbostyril and its 3,4-dehydro compound
1-Benzyl-5-{3-[4-(2-phenylethyl)-1-piperidyl]propoxy}-3,4-dihydrocarbostyril and its 3,4-dehydro compound
1-Benzyl-7-{3-[4-(1-phenylethyl)-1-piperidyl]propoxy}-3,4-dihydrocarbostyril and its 3,4-dehydro compound
1-Methyl-5-{3-[4-(4-phenylbutyl)-1-piperidyl]propoxy}-3,4-dihydrocarbostyril and its 3,4-dehydro compound
1-Methyl-7-{3-[4-(6-phenylhexyl)-1-piperidyl]propoxy}-3,4-dihydrocarbostyril and its 3,4-dehydro compound
8-Bromo-5-[3-(4-benzyl-1-piperidyl)propoxy]-3,4-dihydrocarbostyril and its 3,4-dehydro compound
1-Methyl-5-bromo-6-[3-(4-benzyl-1-piperidyl)propoxy]-3,4-dihydrocarbostyril and its 3,4-dehydro compound
6-Fluoro-7-[3-(4-benzyl-1-piperidyl)propoxy]-3,4-dihydrocarbostyril and its 3,4-dehydro compound
1-Benzyl-6-chloro-5-[3-(4-benzyl-1-piperidyl)ethoxy]-3,4-dihydrocarbostyril and its 3,4-dehydro compound
1-Benzyl-5-chloro-8-[3-(4-benzyl-1-piperidyl)propoxy]-3,4-dihydrocarbostyril and its 3,4-dehydro compound
1-Benzyl-6-chloro-7-[3-(4-benzyl-1-piperidyl)ethoxy]-3,4-dihydrocarbostyril and its 3,4-dehydro compound
6,8-Dichloro-5-[3-(4-benzyl-1-piperidyl)propoxy]-3,4-dihydrocarbostyril and its 3,4-dehydro compound
6-Chloro-8-bromo-7-[3-(4-benzyl-1-piperidyl)propoxy]-3,4-dihydrocarbostyril and its 3,4-dehydro compound
5-[3-(4-Phenyl-1-piperidyl)propoxy]-3,4-dihydrocarbostyril and its 3,4-dehydro compound
6-[3-(4-Phenyl-1-piperidyl)propoxy]-3,4-dihydrocarbostyril and its 3,4-dehydro compound
7-[3-(4-Phenyl-1-piperidyl)propoxy]-3,4-dihydrocarbostyril and its 3,4-dehydro compound
8-[3-(4-Phenyl-1-piperidyl)propoxy]-3,4-dihydrocarbostyril and its 3,4-dehydro compound
1-Methyl-5-[3-(4-phenyl-1-piperidyl)propoxy]-3,4-dihydrocarbostyril and its 3,4-dehydro compound
1-Benzyl-7-[3-(4-phenyl-1-piperidyl)propoxy]-3,4-dihydrocarbostyril and its 3,4-dehydro compound
1-Benzyl-5-[3-(4-phenyl-1-piperidyl)propoxy]-3,4-dihydrocarbostyril and its 3,4-dehydro compound
1-Methyl-7-[3-(4-phenyl-1-piperidyl)propoxy]-3,4-dihydrocarbostyril and its 3,4-dehydro compound
1-Propargyl-7-[3-(4-phenyl-1-piperidyl)propoxy]-3,4-dihydrocarbostyril and its 3,4-dehydro compound
1-Benzyl-6-chloro-5-[3-(4-phenyl-1-piperidyl)propoxy]-3,4-dihyrocarbostyril and its 3,4-dehydro compound
6,8-Dichloro-5-[3-(4-phenyl-1-piperidyl)propoxy]-3,4-dihydrocarbostyril and its 3,4-dehydro compound
1-Benzyl-6,8-dichloro-5-[3-(4-phenyl-1-piperidyl)propoxy]-3,4-dihydrocarbostyril and its 3,4-dehydro compound
1-Methyl-6-chloro-7-[3-(4-phenyl-1-piperidyl)propoxy]-3,4-dihydrocarbostyril and its 3,4-dehydro compound
1-Hexyl-7-[3-(4-phenyl-1-piperidyl)propoxy]-3,4-dihyrocarbostyril and its 3,4-dehydro compound
1-(3-Phenylpropyl)-7-[3-(4-phenyl-B 1-piperidyl)propoxy]-3,4-dihydrocarbostyril and its 3,4-dehydro compound
5-[2-Methyl-3-(4-benzyl-1-piperidyl)propoxy]-3,4-dihydrocarbostyril and its 3,4-dehydro compound
7-[2-Methyl-3-(4-benzyl-1-piperidyl)propoxy]-3,4-dihydrocarbostyril and its 3,4-dehydro compound
7-[2,2-Dimethyl-3-(4-benzyl-1-piperidyl)propoxy]-3,4-dihydrocarbostyril and its 3,4-dehydro compound 1-Methyl-5-[2-methyl-3-(4-benzyl-1-piperidyl)propoxy]-3,4-dihydrocarbostyril and its 3,4-dehydro compound 1-Benzyl-7-[2-methyl-3-(4-benzyl-1-piperidyl)propoxy]-3,4-dihydrocarbostyril and its 3,4-dehydro compound 5-[2-Methyl-(4-phenyl-1-piperidyl)propoxy]-3,4-dihydrocarbostyril and its 3,4-dehydro compound 7-[2-Methyl-4-(phenyl-1-piperidyl)propoxy]-3,4-dihydrocarbostyril and its 3,4-dehydro compound 1-Methyl-5-[2-methyl-3-(4-phenyl-1-piperidyl)propoxy]-3,4-dihydrocarbostyril and its 3,4-dehydro compound 1-Benzyl-7-[2-methyl-3-(4-phenyl-1-piperidyl)propoxy]-3,4-dihydrocarbostyril and its 3,4-dehydro compound 6-Chloro-5-[2-methyl-3-(4-phenyl-1-piperidyl)propoxy]-3,4-dihydrocarbostryl and its 3,4-dehydro compound 4-Methyl-5-[3-(4-benzyl-1-piperidyl)propoxy]-3,4-dihydrocarbostyril and its 3,4-dehydro compound 4-Methyl-6-[3-(4-benzyl-1-piperidyl)propoxy]-3,4-dihydrocarbostyril and its 3,4-dehydro compound 4-Methyl-7-[3-(4-benzyl-1-piperidyl)propoxy]-3,4-dihydrocarbostyril and its 3,4-dehydro compound 1,4-Dimethyl-5-[3-(4-benzyl-1-piperizyl)propoxy]-3,4-dihydrocarbostyril and its 3,4-dehydro compound 1-Benzyl-4-methyl-7-[3-(4-benzyl-1-piperidyl)propoxy]-3,4-dihydrocarbostyril and its 3,4-dehydro compound 4-Methyl-5-[3-(4-phenyl-1-piperidyl)propoxy]-3,4-dihydrocarbostyril and its 3,4-dehydro compound 4-Methyl-7-[3-(4-phenyl-1-piperidyl)propoxy]-3,4-dihydrocarbostyril and its 3,4-dehydro compound 1,4-Dimethyl-7-[3-(4-phenyl-1-piperidyl)propoxy]-3,4-dihydrocarbostyril and its 3,4-dehydro compound 4-Methyl-5-[2-hydroxy-3-(4-benzyl-1-piperidyl)propoxy]-3,4-dihydrocarbostyril and its 3,4-dehydro compound 1-Benzyl-7-[2-hydroxy-3-(4-benzyl-1-piperidyl)propoxy]-3,4-dihydrocarbostyril and its 3,4-dehydro compound 1,4-Dimethyl-5-[2-hydroxy-3-(4-phenyl-1-piperidyl)propoxy]-3,4-dihydrocarbostyril and its 3,4-dehydro compound 7-[2-Hydroxy-3-(4-phenyl-1-piperidyl)propoxy]-3,4-dihydrocarbostyril and its 3,4-dehydro compound 4-Phenyl-5-[3-(4-benzyl-1-piperidyl)propoxy]-3,4-dihydrocarbostyril and its 3,4-dehydro compound 1-Benzyl-4-phenyl-7-[3-(4-benzyl-1-piperidyl)propoxy]-3,4-dihydrocarbostyril and its 3,4-dehydro compound 1-Methyl-4-phenyl-5-[3-(4-phenyl-1-piperidyl)propoxy]-3,4-dihydrocarbostyril and its 3,4-dehydro compound 4-Phenyl-7-[3-(4-phenyl-1-piperidyl)propoxy]-3,4-dihydrocarbostyril and its 3,4-dehydro compound 4-Phenyl-5-[2-hydroxy-3-(4-benzyl-1-piperidyl)propoxy]-3,4-dihydrocarbostyril and its 3,4-dehydro compound 1-Methyl-4-phenyl-7-[2-hydroxy-3-(4-benzyl-1-piperidyl)propoxy]-3,4-dihydrocarbostyril and its 3,4-dehydro compound 4-Phenyl-7-[2-hydroxy-3-(4-phenyl-1-piperidyl)propoxy]-3,4-dihydrocarbostyril and its 3,4-dehydro compound 1-Benzyl-4-phenyl-5-[2-(hydroxy-3-(4-phenyl-1-piperidyl)propoxy]-3,4-dihydrocarbostyril and its 3,4-dehydro compound 6-Cholor-7-{3-[4-(2,3-dimethylphenyl)-1-piperidyl]propoxy}-3,4-dihydrocarbostyril and its 3,4-dehydro compound 5-{3-[4-(2-Fluorophenyl)-1-piperidyl]propoxy}-3,4-dihydrocarbostyril and its 3,4-dehydro compound 7-{3-[4-(3-Chlorophenyl)-1-piperidyl]propoxy}-3,4-dihydrocarbostyril and its 3,4-dehydro compound 6-{3-[4-(4-Chlorophenyl)-1-piperidyl]propoxy}-3,4-dihydrocarbostyril and its 3,4-dehydro compound 7-{3-[4-(3,4-Dichlorophenyl)-1-piperidyl]propoxy}-3,4-dihydrocarbostyril and its 3,4-dehydro compound 7-{3-[4-(2-Fluorophenyl)-1-piperidyl]propoxy}-3,4-dihydrocarbostyril and its 3,4-dehydro compound 5-{3-[4-(2-Methylphenyl)-1-piperidyl]propoxy}-3,4-dihydrocarbostyril and its 3,4-dehydro compound 6-{3-[4-(3-Ethylphenyl)-1-piperidyl]propoxy}-3,4-dihydrocarbostyril and its 3,4-dehydro compound 7-{3-[4-(4-Methylphenyl)-1-piperidyl]propoxy}-3,4-dihydrocarbostyril and its 3,4-dehydro compound 7-{3-[4-(2,3-Dimethylphenyl)-1-piperidyl]propoxy}-3,4-dihydrocarbostyril and its 3,4-dehydro compound 5-{3-[4-(4-Methoxyphenyl)-1-piperidyl]propoxy}-3,4-dihydrocarbostyril and its 3,4-dehydro compound 7-{3-[4-(2-Ethoxyphenyl)-1-piperidyl]propoxy}-3,4-dihydrocarbostyril and its 3,4-dehydro compound 8-{3-[4-(3-Methoxyphenyl)-1-piperidyl]propoxy}-3,4-dihydrocarbostyril and its 3,4-dehydro compound 7-{3-[4-(3,4-Dimethoxyphenyl)-1-piperidyl]propoxy}-3,4-dihydrocarbostyril and its 3,4-dehydro compound 7-{3-[4-(3,4,5-Trimethoxyphenyl)-1-piperidyl]propoxy}-3,4-dihydrocarbostyril and its 3,4-dehydro compound 7-{3-[4-(2-Chlorophenyl)-1-piperidyl]propoxy}-3,4-dihydrocarbostyril and its 3,4-dehydro compound 5-{3-[4-(4-Fluorophenyl)-1-piperidyl]propoxy}-3,4-dihydrocarbostyril and its 3,4-dehydro compound 5-{3-[4-(3-Methylphenyl)-1-piperidyl]propoxy}-3,4-dihydrocarbostyril and its 3,4-dehydro compound 7-{3-[4-(2-Methoxyphenyl)-1-piperidyl]propoxy}-3,4-dihydrocarbostyril and its 3,4-dehydro compound 5-{2-Hydroxy-3-[4-(2-fluorophenyl)-1-piperidyl]propoxy}-3,4-dihydrocarbostyril and its 3,4-dehydro compound 7-{2-Hydroxy-3-[4-(4-chlorophenyl)-1-piperidyl]propoxy}-3,4-dihydrocarbostyril and its 3,4-dehydro compound 7-{2-Hydroxy-3-[4-(2-methoxyphenyl)-1-piperidyl]propoxy}-3,4-dihydrocarbostyril and its 3,4-dehydro compound 7-{2-Hydroxy-3-[4-(3,4,5-trimethoxyphenyl)-1-piperidyl]propoxy}-3,4-dihydrocarbostyril and its 3,4-dehydro compound 7-{2-Hydroxy-3-[4-(2-methylphenyl)-1-piperidyl]propoxy}-3,4-dihydrocarbostyril and its 3,4-dehydro compound 7-{2-Hydroxy-3-[4-(2,3-dimethylphenyl)-1-piperidyl]propoxy}-3,4-dihydrocarbostyril and its 3,4-dehydro compound 7-{2-Hydroxy-3-[4-(3-methylphenyl)-1-piperidyl]propoxy}-3,4-dihydrocarbostyril and its 3,4-dehydro compound 4-Methyl-7-{3-[4-(2-chlorophenyl)-1-piperidyl]propoxy}-3,4-dihydrocarbostyril and its 3,4-dehydro compound 4-Methyl-5-{3-[4-(3-methoxyphenyl)-1-piperidyl]propoxy}-3,4-dihydrocarbostyril and its 3,4-dehydro compound 4-{Methyl-7-{2-hydroxy-3-[4-(2-methoxyphenyl)-1-piperidyl]propoxy}-3,4-dihydrocarbostyril and its 3,4-dehydro compound 5-{3-[4-(2-Fluorophenyl)-1-piperidyl]-propoxy}-3,4-dihydrocarbostyril and its 3,4-dehydro compound 7-{3-[4-(4-Fluorophenyl)-1-piperidyl]-propoxy}-3,4-dihydrocarbostyril and its 3,4-dehydro compound 5-{3-[4-(3-Methylphenyl)-1-piperidyl]-propoxy}-3,4-dihydrocarbostyril and its 3,4-dehydro compound 7-{3-[4-(3-Methoxyphenyl)-1-piperidyl]-propoxy}-3,4-dihydrocarbostyril and its 3,4-dehydro compound 5-{2-Hydroxy-3-[4-(2-fluorophenyl)-1-piperidyl]-propoxy}-3,4-dihydrocarbostyril and its 3,4-dehydro compound 7-{2-Hydroxy-3-[4-(2-methoxyphenyl)-1-piperidyl]-propoxy}-3,4-dihydrocarbostyril and its 3,4-dehydro compound 7-{2-Hydroxy-3-[4-(3-chlorophenyl)-1-piperidyl]-propoxy}-3,4-dihydrocarbostyril and its 3,4-dehydro compound 4-Phenyl-1-[3-(2-oxo-1,2,3,4-tetrahydroquinolin-7-yloxy)propyl]-1-methylpiperidiniumiodide 4-Phenyl-1-[3-(2-oxo-1,2,3,4-tetrahydroquinolin-5-yloxy)propyl]-1-methylpiperidiniumiodide 4-Phenyl-1-[3-(1-methyl-2-oxo-1,2,3,4-tetrahydroquinolin-7-yloxy)propyl]-1-methylpiperidiniumiodide 4-Phenyl-1-[3-(1-allyl-2-oxo-1,2,3,4-tetrahydroquinolin-7-yloxy)propyl]-1-methylpiperidiniumiodide 4-Phenyl-1-[3-(1-benzyl-2-oxo-1,2,3,4-tetrahydroquinolin-5-yloxy)propyl]-1-ethylpiperidiniumchloride 4-Phenyl-1-[3-(1-propargyl-2-oxo-1,2,3,4-tetrahydroquinolin-5-yloxy)propyl]-1-methylpiperidiniumchloride 4-Phenyl-1-[3-(6-chloro-2-oxo-1,2,3,4-tetrahydroquinolin-7-yloxy)propyl]-1-methylpiperidiniumchloride.

4-(2-Fluorophenyl)-1-[3-(2-oxo-1,2,3,4-tetrahydroquinolin-5-yloxy)propyl]-1-methylpiperidiniumchloride 4-(3-Chlorophenyl)-1-[3-(2-oxo-1,2,3,4-tetrahydroquinolin-7-yloxy)propyl]-1-methylpiperidiniumiodide 4-(3,4-Dichlorophenyl)-1-[3-(2-oxo-1,2,3,4-tetrahydroquinolin-7-yloxy)propyl]-1-methylpiperidiniumiodide 4-(2-Methylphenyl)-1-[3-(2-oxo-1,2,3,4-tetrahydroquinolin-5-yloxy)propyl]-1-methylpiperidiniumiodide 4-(4-Methylphenyl)-1-[3-(2-oxo-1,2,3,4-tetrahydroquinolin-7-yloxy)propyl]-1-methylpiperidiniumchloride 4-(2,3-Dimethylphenyl)-1-[3-(2-oxo-1,2,3,4-tetrahydroquinolin-7-yloxy)propyl]-1-methylpiperidiniumchloride 4-(4-Methoxyphenyl)-1-[3-(2-oxo-1,2,3,4-tetrahydroquinolin-5-yloxy)propyl]-1-methylpiperidiniumchloride 4-(2-Methoxyphenyl)-1-[3-(2-oxo-1,2,3,4-tetrahydroquinolin-7-yloxy)propyl]-1-methylpiperidiniumiodide 4-(3,4-Dimethoxyphenyl)-1-[3-(2-oxo-1,2,3,4-tetrahydroquinolin-7-yloxy)propyl]-1-methylpiperidiniumiodide 4-(3,4,5-Trimethoxyphenyl)-1-[3-(2-oxo-1,2,3,4-tetrahydroquinolin-7-yloxy)propyl]-1-methylpiperidiniumchloride 4-Benzyl-1-[3-(2-oxo-1,2,3,4-tetrahydroquinolin-5-yloxy)propyl]-1-methylpiperidiniumiodide 4-Benzyl-1-[3-(2-oxo-1,2,3,4-tetrahydroquinolin-7-yloxy)propyl]-1-methylpiperidiniumchloride 4-Phenyl-1-[3-(2-oxo-1,2-dihydroquinolin-7-yloxy)-propyl]-1-methylpiperidiniumiodide 4-(4-Fluorophenyl)-1-[3-(2-oxo-1,2-dihydroquinolin-7-yloxy)propyl]-1-methylpiperidiniumiodide 4-(3-Methylphenyl)-1-[3-(2-oxo-1,2-dihydroquinolin-5-yloxy)propyl]-1-methylpiperidiniumiodide 4-(3-Methoxyphenyl)-1-[3-(2-oxo-1,2-dihydroquinolin-7-yloxy)propyl]-1-methylpiperidiniumchloride 4-Benzyl-1-[3-(2-oxo-1,2-dihydroquinolin-7-yloxy)-propyl]-1-methylpiperdiniumiodide 4-Phenyl-1-[2-hydroxy-3-(2-oxo-1,2,3,4-tetrahydroquinolin-5-yloxy)propyl]-1-methylpiperidiniumiodide 4-Phenyl-1-[2-hydroxy-3-(2-oxo-1,2,3,4-tetrahydroquinolin-7-yloxy)propyl]-1-methylpiperidiniumchloride 4-Phenyl-1-[2-hydroxy-3-(1-methyl-2-oxo-1,2,3,4-tetrahydroquinolin-7-yloxy)propyl]-1-methylpiperidiniumiodide 4-Phenyl-1-[2-hydroxy-3-(1-benzyl-2-oxo-1,2,3,4-tetrahydroquinolin-5-yloxy)propyl]-1-methylpiperidiniumiodide 4-Phenyl-1-[2-hydroxy-3-(6-chloro-2-oxo-1,2,3,4-tetrahydroquinolin-7-yloxy)propyl]-1-methylpiperidiniumiodide 4-Phenyl-1-[2-hydroxy-3-(6,8-dibromo-2-oxo-1,2,3,4-tetrahydroquinolin-5-yloxy)propyl]-1-methylpiperidiniumchloride 4-(2-Fluorophenyl)-1-[2-hydroxy-3-(2-oxo-1,2,3,4-tetrahydroquinolin-5-yloxy)propyl]-1-methylpiperidiniumiodide 4-(2-Methoxyphenyl)-1-[2-hydroxy-3-(2-oxo-1,2,3,4-tetrahydroquinolin-7-yloxy)propyl]-1-methylpiperidiniumchloride 4-(2,3-Dimethylphenyl)-1-[2-hydroxy-3-(2-oxo-1,2,3,4-tetrahydroquinolin-7-yloxy)propyl]-1-methylpiperidiniumchloride 4-(3-Chlorophenyl)-1-[2-hydroxy-3-(2-oxo-1,2-dihydroquinolin-7-yloxy)propyl]-1-methylpiperidiniumiodide 4-(4-Methoxyphenyl)-1-[2-hydroxy-3-(2-oxo-1,2-dihydroquinolin-5-yloxy)propyl]-1-methylpiperidiniumiodide 4-(2-Methylphenyl)-1-[2-hydroxy-3-(2-oxo-1,2-dihydroquinolin-7-yloxy)propyl]-1-methylpiperidiniumiodide 4-Hydroxy-4-phenyl-1-[2-hydroxy-3-(2-oxo-1,2,3,4-tetrahydroquinolin-5-yloxy)propyl]-1-methylpiperidiniumiodide 4-Acetyl-4-phenyl-1-[3-(2-oxo-1,2,3,4-tetrahydroquinolin-5-yloxy)propyl]-1-methylpiperidiniumiodide 4-Hydroxy-4-phenyl-1-[2-hydroxy-3-(2-oxo-1,2,3,4-tetrahydroquinolin-7-yloxy)propyl]-1-methylpiperidiniumiodide 4-Acetyl-4-phenyl-1-[3-(2-oxo-1,2,3,4-tetrahydroquinolin-7-yloxy)propyl]-1-methylpiperidiniumiodide 5-[3-(4-Hydroxy-4-phenyl-1-piperidyl)propoxy]-3,4-dihydrocarbostyril and its 3,4-dehydro compound 5-{3-[4-Hydroxy-4-(4-chlorophenyl)-1-piperidyl]-propoxy}-3,4-dihydrocarbostyril and its 3,4-dehydro compound 5-{3-[4-Hydroxy-4-(4-fluorophenyl)-1-piperidyl]-propoxy}-3,4-dihydrocarbostyril and its 3,4-dehydro compound 5-{3-[4-Hydroxy-4-(2-fluorophenyl)-1-piperidyl]-propoxy}-3,4-dihydrocarbostyril and its 3,4-dehydro compound 5-{3-[4-Hydroxy-4-(2-chlorophenyl)-1-piperidyl]-propoxy}-3,4-dihydrocarbostyril and its 3,4-dehydro compound 5-{3-[4-Hydroxy-4-(3-chlorophenyl)-1-piperidyl]-propoxy}-3,4-dihydrocarbostyril and its 3,4-dehydro compound 5-{3-[4-Hydroxy-4-(4-bromophenyl)-1-piperidyl]-propoxy}-3,4-dihydrocarbostyril and its 3,4-dehydro compound 5-{3-[4-Hydroxy-4-(2,6-dichlorophenyl)-1-piperidyl]-propoxy}-3,4-dihydrocarbostyril and its 3,4-dehydro compound 5-{3-[4-Hydroxy-4-(3-fluorophenyl)-1-piperidyl]-propoxy}-3,4-dihydrocarbostyril and its 3,4-dehydro compound 5-{3-[4-Hydroxy-4-(3-bromophenyl)-1-piperidyl]-propoxy}-3,4-dihydrocarbostyril and its 3,4-dehydro compound 5-{3-[4-Hydroxy-4-(2-bromophenyl-1-piperidyl]-propoxy}-3,4-dihydrocarbostyril and its 3,4-dehydro compound 5-{3-[4-Hydroxy-4-(4-iodophenyl)-1-piperidyl]-propoxy}-3,4-dihydrocarbostyril and its 3,4-dehydro compound 5-[1-(4-Hydroxy-4-phenyl-1-piperidyl)methoxy]-3,4-dihydrocarbostyril and its 3,4-dehydro compound 5-[2-(4-Hydroxy-4-phenyl-1-piperidyl)ethoxy]-3,4-dihydrocarbostyril and its 3,4-dehydro compound 5-[3-(4-Acetyl-4-phenyl-1-piperidyl)propoxy]-3,4-dihydrocarbostyril and its 3,4-dehydro compound 5-[3-(4-Propionyl-4-phenyl-1-piperidyl)propoxy]-3,4-dihydrocarbostyril and its 3,4-dehydro compound 5-[3-(4-Hexanoyl-4-phenyl-1-piperidyl)propoxy]-3,4-dihydrocarbostyril and its 3,4-dehydro compound 1-Benzyl-5-[2-(4-hydroxy-4-phenyl-1-piperidyl)ethoxy]-3,4-dihydrocarbostyril and its 3,4-dehydro compound 5-[4-(4-Hydroxy-4-phenyl-1-piperidyl)butoxy]-3,4-dihydrocarbostyril and its 3,4-dehydro compound 6-[3-(4-Hydroxy-4-phenyl-1-piperidyl)propoxy]-3,4-dihydrocarbostyril and its 3,4-dehydro compound 6-{3-[4-Hydroxy-4-(4-chlorophenyl)-1-piperidyl]-propoxy}-3,4-dihydrocarbostyril and its 3,4-dehydro compound 6-{3-[4-Hydroxy-4-(4-fluorophenyl)-1-piperidyl]-propoxy}-3,4-dihydrocarbostyril and its 3,4-dehydro compound 6-{3-[4-Hydroxy-4-(2-fluorophenyl)-1-piperidyl]-propoxy}-3,4-dihydrocarbostyril and its 3,4-dehydro compound 6-{3-[4-Hydroxy-4-(2-chlorophenyl)-1-piperidyl]-propoxy}-3,4-dihydrocarbostyril and its 3,4-dehydro compound 6-{3-[4-Hydroxy-4-(3-chlorophenyl)-1-piperidyl]-propoxy}-3,4-dihydrocarbostyril and its 3,4-dehydro compound 6-{3-[4-Hydroxy-4-(4-bromophenyl)-1-piperidyl]-propoxy}-3,4-dihydrocarbostyril and its 3,4-dehydro compound 6-{3-[4-Hydroxy-4-(2,6-dichlorophenyl)-1-piperidyl]-propoxy}-3,4-dihydrocarbostyril and its 3,4-dehydro compound 6-{3-[4-Hydroxy-4-(3-fluorophenyl)-1-piperidyl]-propoxy}-3,4-dihydrocarbostyril and its 3,4-dehydro compound 6-{3-[4-Hydroxy-4-(3-bromophenyl)-1-piperidyl]-propoxy}-3,4-dihydrocarbostyril and its 3,4-dehydro compound 6-{3-[4-Hydroxy-4-(2-bromophenyl)-1-piperidyl]-propoxy}-3,4-dihydrocarbostyril and its 3,4-dehydro compound 6-{3-[4-Hydroxy-4-(4-iodophenyl)-1-piperidyl]propoxy}-3,4-dihydrocarbostyril and its 3,4-dehydro compound 6-[3-(4-Acetyl-4-phenyl-1-piperidyl)propoxy]-3,4-dihydrocarbostyril and its 3,4-dehydro compound 6-[3-(4-Propionyl-4-phenyl-1-piperidyl)propoxy]-3,4-dihydrocarbostyril and its 3,4-dehydro compound 6-[3-(4-Hexanoyl-4-phenyl-1-piperidyl)propoxy]-3,4-dihydrocarbostyril and its 3,4-dehydro compound 7-[3-(4-Hydroxy-4-phenyl-1-piperidyl)propoxy]-3,4-dihydrocarbostyril and its 3,4-dehydro compound 7-{3-[4-Hydroxy-4-(4-chlorophenyl)-1-piperidyl]-propoxy}-3,4-dihydrocarbostyril and its 3,4-dehydro compound 7-{3-[4-Hydroxy-4-(4-fluorophenyl)-1-piperidyl]-propoxy}-3,4-dihydrocarbostyril and its 3,4-dehydro compound 7-{3-[4-Hydroxy-4-(2-fluorophenyl)-1-piperidyl]-propoxy}-3,4-dihydrocarbostyril and its 3,4-dehydro compound 7-{3-[4-Hydroxy-4-(2-chlorophenyl)-1-piperidyl]-propoxy}-3,4-dihydrocarbostyril and its 3,4-dehydro compound 7-{3-[4-Hydroxy-4-(3-chlorophenyl)-1-piperidyl]-propoxy}-3,4-dihydrocarbostyril and its 3,4-dehydro compound 7-{3-[4-Hydroxy-4-(4-bromophenyl)-1-piperidyl]-propoxy}-3,4-dihydrocarbostyril and its 3,4-dehydro compound 6-[2-(4-Acetyl-4-phenyl-1-piperidyl)ethoxy]-3,4-dihydrocarbostyril and its 3,4-dehydro compound 7-{3-[4-Hydroxy-4-(2,6-dichlorophenyl)-1-piperidyl]-propoxy}-3,4-dihydrocarbostyril and its 3,4-dehydro compound 7-{3-[4-Hydroxy-4-(3-fluorophenyl)-1-piperidyl]-propoxy}-3,4-dihydrocarbostyril and its 3,4-dehydro compound 7-{3-[4-Hydroxy-4-(3-bromophenyl)-1-piperidyl]-propoxy}-3,4-dihydrocarbostyril and its 3,4-dehydro compound 7-{3-[4-Hydroxy-4-(2-bromophenyl)-1-piperidyl]-propoxy}-3,4-dihydrocarbostyril and its 3,4-dehydro compound 7-{3-[4-Hydroxy-4-(4-iodophenyl)-1-piperidyl]propoxy}-3,4-dihydrocarbostyril and its 3,4-dehydro compound 8-[3-(4-Hydroxy-4-phenyl-1-piperidyl)propoxy]-3,4-dihydrocarbostyril and its 3,4-dehydro compound 8-{3-[4-Hydroxy-4-(4-chlorophenyl)-1-piperidyl]-propoxy}-3,4-dihydrocarbostyril and its 3,4-dehydro compound 8-{3-[4-Hydroxy-4-(4-fluorophenyl)-1-piperidyl]-propoxy}-3,4-dihydrocarbostyril and its 3,4-dehydro compound 8-{3-[4-Hydroxy-4-(2-fluorophenyl)-1-piperidyl]-propoxy}-3,4-dihydrocarbostyril and its 3,4-dehydro compound 8-{3-[4-Hydroxy-4-(2-chlorophenyl)-1-piperidyl]-propoxy}-3,4-dihydrocarbostyril and its 3,4-dehydro compound 8-{3-[4-Hydroxy-4-(3-chlorophenyl)-1-piperidyl]-propoxy}-3,4-dihydrocarbostyril and its 3,4-dehydro compound 8-{3-[4-Hydroxy-4-(4-bromophenyl)-1-piepridyl]-propoxy}-3,4-dihydrocarbostyril and its 3,4-dehydro compound 7-[3-(4-Acetyl-4-phenyl-1-piperidyl)propoxy]-3,4-dihydrocarbostyril and its 3,4-dehydro compound 7-[3-(4-Propionyl-4-phenyl-1-piperidyl)propoxy]-3,4-dihydrocarbostyril and its 3,4-dehydro compound 7-[3-(4-Hexanoyl-4-phenyl-1-piperidyl)propoxy]-3,4-dihydrocarbostyril and its 3,4-dehydro compound 7-[2-(4-Hydroxy-4-phenyl-1-piperidyl)ethoxy]-3,4-dihydrocarbostyril and its 3,4-dehydro compound 7-[6-(4-Hydroxy-4-phenyl-1-piperidyl)hexyloxy]-3,4-dihydrocarbostyril and its 3,4-dehydro compound 8-{3-[4-Hydroxy-4-(2,6-dichlorophenyl)-1-piperidyl]-propoxy}-3,4-dihydrocarbostyril and its 3,4-dehydro compound 8-{3-[4-Hydroxy-4-(3-fluorophenyl)-1-piperidyl]-propoxy}-3,4-dihydrocarbostyril and its 3,4-dehydro compound 8-{3-[4-Hydroxy-4-(3-bromophenyl)-1-piperidyl]-propoxy}-3,4-dihydrocarbostyril and its 3,4-dehydro compound 8-{3-[4-Hydroxy-4-(2-bromophenyl)-1-piperidyl]-propoxy}-3,4-dihydrocarbostyril and its 3,4-dehydro compound 8-{3-[4-Hydroxy-4-(4-iodophenyl)-1-piperidyl]-propoxy}-3,4-dihydrocarbostyril and its 3,4-dehydro compound 8-[3-(4-Acetyl-4-phenyl-1-piperidyl)propoxy]-3,4-dihydrocarbostyril and its 3,4-dehydro compound 8-[3-(4-Propionyl-4-phenyl-1-piperidyl)propoxy]-3,4-dihydrocarbostyril and its 3,4-dehydro compound 8-{3-(4-Hexanoyl-4-phenyl-1-piperidyl)propoxy]-3,4-dihydrocarbostyril and its 3,4-dehydro compound 7-[2-Hydroxy-3-(4-acetyl-4-phenyl-1-piperidyl)propoxy]-3,4-dihydrocarbostyril and its 3,4-dehycro compound 8-[2-Hydroxy-3-(4-acetyl-4-phenyl-1-piperidyl)propoxy]-3,4-dihydrocarbostyril and its 3,4-dehydro comound 5-{2-Hydroxy-3-[4-hydroxy-(4-chlorophenyl)-1-piperidyl]propoxy}-3,4-dihydrocarbostyril and its 3,4-dehydro compound 1-Benzyl-5-[2-hydroxy-3-(4-hydroxy-4-phenyl-1-piperidyl)propoxy]-3,4-dihydrocarbostyril and its 3,4-dehydro compound 6-{2-Hydroxy-3-[4-acetyl-4-(3-methoxyphenyl)-1-piperidyl]propoxy}-3,4-dihydrocarbostyril and its 3,4-dehydro compound 5-{2-Hydroxy-3-[4-acetyl-4-(2,3-dimethylphenyl)-1-piperidyl]propoxy}-3,4-dihydrocarbostyril and its 3,4-dehydro compound 5-[2-Hydroxy-3-(4-acetyl-4-phenyl-1-piperidyl)propoxy]-4-methyl-3,4-dihydrocarbostyril and its 3,4-dehydro compound 7-[2-Hydroxy-3-(4-acetyl-4-phenyl-1-piperidyl)propoxy]-4-phenyl-3,4-dihydrocarbostryril and its 3,4-dehydro compound 5-[2-Hydroxy-3-(4-hydroxy-4-phenyl-1-piperidyl)propoxy]-4-methyl-3,4-dihydrocarbostyril and its 3,4-dehydro compound 5-[3-(4-Hydroxy-4-phenyl-1-piperidyl)propoxy]-4-methyl-3,4-dihydrocarbostyril and 3,4-dehydro compound 7-[3-(4-Acetyl-4-phenyl-1-piperidyl)propoxy]-4-phenyl-3,4-dihydrocarbostyril and its 3,4-dehydro compound 5-[2-Hydroxy-3-(4-acetyl-4-phenyl-1-piperidyl)propoxy]-3,4-dihydrocarbostyril and its 3,4-dehydro compound 1-Methyl-5-[2-hydroxy-3-(4-acetyl-4-phenyl-1-piperidyl)propoxy]-3,4-dihydrocarbostyril and its 3,4-dehydro compound 1-Benzyl-7-[2-hydroxy-3-(4-acetyl-4-phenyl-1-piperidyl)propoxy]-3,4-dihydrocarbostyril and its 3,4-dehydro compound 1-Methyl-5-[2-hydroxy-3-(4-hydroxy-4-phenyl-1-piperidyl)propoxy]-3,4-dihydrocarbostyril and its 3,4-dehydro compound 5-[3-Hydroxy-4-(4-acetyl-4-phenyl-1-piperidyl)butoxy]-3,4-dihydrocarbostyril and its 3,4-dehydro compound 7-[2-Hydroxy-4-(4-hydroxy-4-phenyl-1-piperidyl)-butoxy]-3,4-dihydrocarbostyril and its 3,4-dehydro compound 5-{2-Hydroxy-3-[4-hydroxy-4-(2,6-dichlorophenyl)-1-piperidyl]propoxy}-3,4-dihydrocarbostyril and its 3,4-dehydro compound 1-Methyl-5-[3-(4-hydroxy-4-phenyl-1-piperidyl)-propoxy]-3,4-dihydrocarbostyril and its 3,4-dehydro compound 1-Benzyl-7-[3-(4-acetyl-4-phenyl-1-piperidyl)propoxy]-3,4-dihydrocarbostyril and its 3,4-dehydro compound 1-Allyl-5-[3-(4-acetyl-4-phenyl-1-piperidyl)propoxy]-3,4-dihydrocarbostyril and its 3,4-dehydro compound 1-Propinyl-7-[3-(4-hydroxy-4-phenyl-1-piperidyl)-propoxy]-3,4-dihydrocarbostyril and its 3,4-dehydro compound 1-(4-Phenylbutyl)-5-[3-(4-hydroxy-4-phenyl-1-piperidyl)propoxy]-3,4-dihydrocarbostyril and its 3,4-dehydro compound 1-Butyl-7-[3-(4-acetyl-4-phenyl-1-piperidyl)propoxy]-3,4-dihydrocarbostyril and its 3,4-dehydro compound 1-Crotyl-7-[3-(4-hydroxy-4-phenyl-1-piperidyl)propoxy]-3,4-dihydrocarbostyril and its 3,4-dehydro compound The compounds of the present invention can be prepared by various processes such as for example the following reaction process formula-1:

REACTION PROCESS FORMULA-1

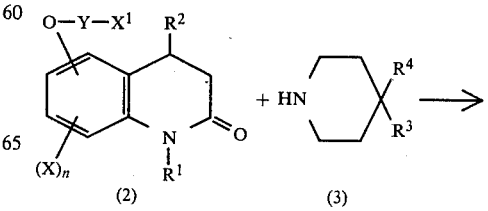

-continued

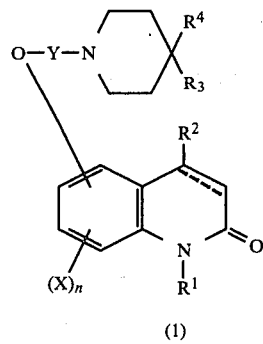

(1)

wherein $R^1$, $R^2$, $R^3$, $R^4$, X, Y, n and the carbon-carbon bond between 3- and 4-positions in the carbostyril skeleton are the same as defined above; and $X^1$ is a halogen atom.

Thus the compound represented by the general formula (1) is prepared by reacting a compound represented by the general formula (2) with a known piperidine derivative represented by the general formula (3). The reaction can be completed in the absence or presence of an inert solvent at from room temperature to about 200° C., preferably at a temperature condition ranging from 60° to 120° C., for several hours to 24 hours.

As to the inert solvent, there is not any specific restriction thereto and any solvent which may not give any adverse effect to the reaction can be used, for example, an ether such as dioxane, tetrahydrofuran (THF), ethylene glycol dimethyl ether, etc.; an aromatic hydrocarbon such as benzene, toluene, xylene, etc.; a lower alcohol such as methanol, ethanol, isopropanol, etc.; and an aprotic polar solvent such as dimethylformamide (DMF), dimethylsulfoxide (DMSO), etc. can be exemplified. The reaction can advantageously be effected by using a basic compound as a dehydrohalogenating agent. As to the basic compound, there is not any specific restriction thereto and any basic compound can be used, for example, potassium carbonate, sodium carbonate, sodium hydroxide, sodium hydrogen-carbonate, sodium amide, sodium hydride, a tertiary amine such as triethylamine, tripropylamine, pyridine, quinoline or the like. The said reaction can also be effected by using an alkali metal iodide for example potassium iodide or sodium iodide as a reaction accelerator. The ratio of the amount of a compound represented by the general formula (2) to the amount of a compound represented by the general formula (3) in the above reaction is usually desirable that the latter is used in an equimolar to an excess quantity, preferably an equimolar to 5 times the molar quantity of the former, more preferably an equimolar to 1.2 times the molar quantity of the former.

The compounds represented by the general formula (2) used as the starting materials in the reaction process formula-1 include novel compounds and these compounds can be prepared by the following reaction process formulas-2 and 3.

REACTION PROCESS FORMULA-2

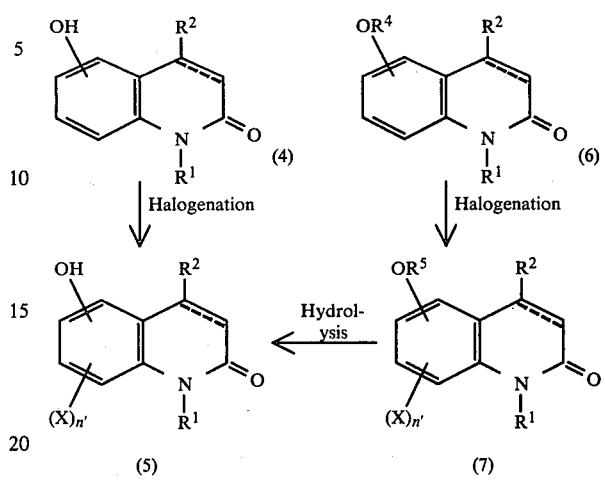

wherein $R^1$, $R^2$, $R^4$, X and the carbon-carbon bond between 3- and 4-positions in the carbostyril skeleton are the same as defined above; $R^5$ is a lower alkyl group or a lower alkanoyl group and n' is 1 or 2.

REACTION PROCESS FORMULA-3

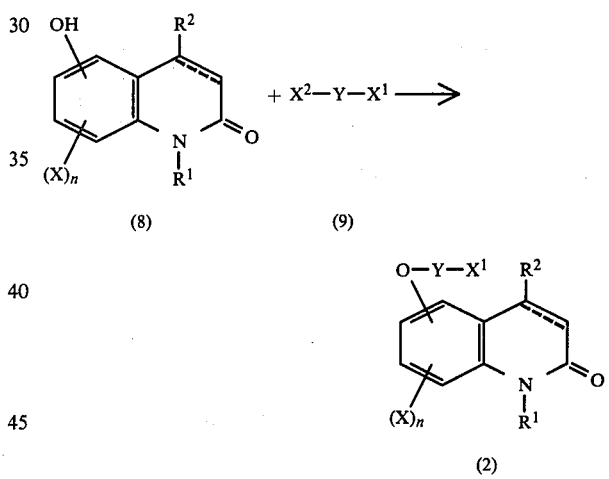

wherein $R^1$, $R^2$, X, $X^1$, Y, n and the carbon-carbon bond between 3- and 4-positions in the carbostyril skeleton are the same as defined above; and $X^2$ is a halogen atom.

In the reaction process formula-2, a compound represented by the general formula (5) can be obtained by reacting a hydroxycarbostyril compound represented by the general formula (4) with a halogenating agent, or hydrolyzing a compound represented by the general formula (7) which is prepared by reacting an alkoxy- or alkanoyloxy-carbostyril compound represented by the general formula (6) with a halogenating agent. The halogenation reaction mentioned above can be carried out by using a known halogenating agent for example, fluorine, chlorine, bromine, iodine, xenon difluoride, sulfuryl chloride, sodium hypochlorite, hypochlorous acid, hypobromous acid, bleaching powder, iodine chloride or the like. The amount of the halogenating agent may suitably be selected from a wide range in accordance with the number of the halogen atoms to be introduced into the starting compound of (4) or (6). In case of introducing one halogen atom, the halogenating agent is usually used in an equimolar or excess amount, preferably, 1 to 1.5 times the molar quantity of the starting compound. In case of introducing two halogen atoms, said halogenating agent is used in an amount of 2 times the moles to large excess, preferably 2 to 3 times the moles of the respective starting compounds. Said halogenation reaction is usually conducted in a suitable solvent such as for example, water, methanol, ethanol, chloroform, carbon tetrachloride, acetic acid or a mixture thereof. The reaction temperature is not subjected to any particular restriction but usually the reaction is carried out at a temperature ranging from $-20°$ to about 100° C., preferably from 0° C. to room temperature. The reaction is completed within a period of about 30 minutes to 20 hours.

The hydrolysis reaction of a compound represented by the general formula (7) varies in accordance with the type of $R^5$ in the formula (7), for example, when $R^5$ is a lower alkanoyl group, the hydrolysis reaction can be carried out under a condition of an usual hydrolysis reaction of an ester. Specifically, the hydrolysis can advantageously be carried out in the presence of a basic compound such as sodium hydroxide, potassium hydroxide, barium hydroxide, sodium carbonate, potassium hydrogencarbonate; a mineral acid such as sulfuric acid or hydrochloric acid; an organic acid such as acetic acid, an aromatic sulfonic acid, in the presence of an usual inert solvent such as water, methanol, ethanol, acetone, dioxane, tetrahydrofuran or benzene. The reaction temperature is usually a room temperature to about 150° C., preferably at 50° to 100° C. The reaction is completed within 1 to about 12 hours. Alternatively, when $R^4$ is a lower alkyl group, the hydrolysis reaction can be carried out under an usual hydrolysis condition of ether. Specifically, the reaction can be carried out by using aluminum chloride, boron trifluoride, boron tribromide, hydrobromic acid or trimethylsilylchloride as a catalyst and in a suitable solvent such as water, methanol, ethanol, benzene, methylene chloride, chloroform or the like at a temperature in the range from 0° to about 200° C., preferably at from room temperature to 120° C., for several hours to about 12 hours. In both hydrolysis reactions, the amount of the catalyst used is not subjected to any specific restriction and usually is used in an excess amount to the starting compound to be hydrolyzed.

In the reaction process formula-3, the desired compound represented by the general formula (2) can be obtained by reacting a compound represented by the general formula (8) with a compound represented by the general formula (9). The reaction can be carried out by using a basic compound as a dehydrohalogenating agent, in a suitable solvent, at from room temperature to about 200° C., preferably at 50° to 150° C., for from several hours to about 15 hours. As to the solvent, there is not any specific restriction thereto and any solvent which may not give any adverse effect to the reaction can be used, the example including the above-mentioned lower alcohols, ethers, aromatic hydrocarbons, dimethylformamide, dimethylsulfoxide or the like, and ketones such as acetone, methylethylketone or the like. As to the dehydrohalogenating agent, there is not any specific restriction thereto and a usual basic compound can be used, for example, the above-mentioned basic compounds and further sodium methoxide, sodium ethoxide, potassium ethoxide, metallic potassium or the like can be used. In the above reaction, an alkali metal iodide such as sodium iodide, potassium iodide or the like can be used as a reaction accelerator. The ratio of the amount of a compound represented by the general formula (8) to the amount of a compound represented by the general formula (9) is not specifically restricted, but it is desirable that the latter is used in equimolar quantity or more, usually 1 to 1.5 times, preferably 1 to 1.2 times the molar quantity of the former. A compound represented by the general formula (2) which is used as the starting material in the present invention can thus be obtained.

In the reaction process formulas-2 and -3, among compounds represented by the general formulas (4), (6) and (8), which are the starting materials used in the reactions, those having substituted group wherein $R^1$ is other than a hydrogen atom include novel compounds. Said compounds can easily be prepared by using a known hydroxycarbostyril, in which $R^1$ is a hydrogen atom, as the starting material and reacting it with a halide in the presence of a basic compound such as an alkali metal, for example sodium metal or potassium metal, an alkali metal amide such as sodium amide or potassium amide, or sodium hydride, in a suitable solvent such as benzene, tetrahydrofuran, dioxane, dimethylsulfoxide, dimethylformamide, hexamethylphosphoryl triamide, at a temperature of from 0° to about 70° C., preferably from 0° C. to room temperature, for about 30 minutes to 12 hours, then hydrolyzing the thus formed compound under a condition similar to that of hydrolysis of the lower alkyl group of the compound represented by the general formula (7), shown in reaction process formula-2. In the above reaction, the ratio of the amounts of the basic compound and the halide to the amount of the starting compound can be suitably selected from a wide range, but usually used in an amount of 2 to about 10 times the moles, preferably 2 to 4 times the moles, of the starting material.

REACTION PROCESS FORMULA-4

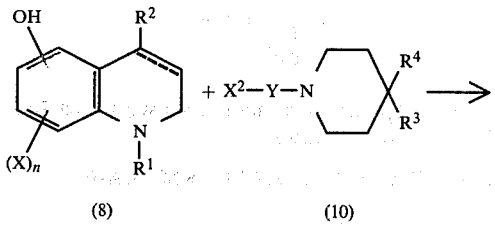

(8)    (10)

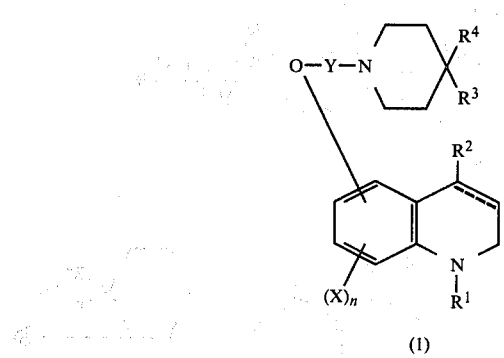

(1)

wherein $R^1$, $R^2$, $R^3$, $R^4$, X, $X^2$, Y, n and the carbon-carbon bond between 3- and 4-positions in the carbostyril skeleton are the same as defined above.

By reacting a hydroxycarbostyril derivative represented by the general formula (8) with a compound represented by the general formula (10), the disired compound of the present invention can be prepared. The reaction conditions in the above reaction process formula-4 are similar to those used in the dehydrohalogenation in the reaction process formula-3 mentioned above.

Among the compounds represented by the general formula (10) used in the above mentioned reaction process formula-4, there are included some novel compounds. Said compounds can easily be prepared by a method of reaction process formula-5 as follows:

REACTION PROCESS FORMULA-5

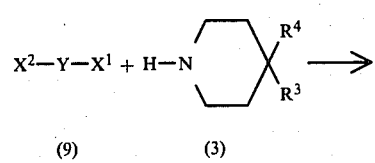

(9)     (3)

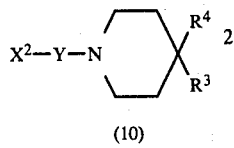

(10)

wherein $X^1$, $X^2$, Y, $R^3$ and $R^4$ are the same as defined above.

The reaction can be carried out under the conditions similar to those used in the reaction of a compound represented by the general formula (2) with a compound represented by the general formula (3) in the reaction process formula-1 mentioned above.

Furthermore, among the compounds represented by the general formula (1), a compound having a group of the formula

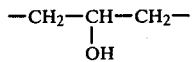

for Y can be prepared by a method shown in reaction process formula-6 as follows.

REACTION PROCESS FORMULA-6

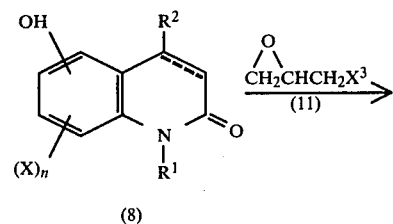

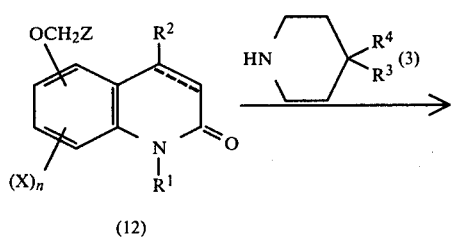

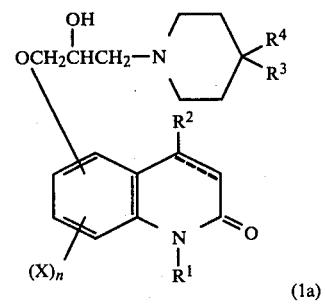

(1a)

wherein $R^1$, $R^2$, $R^3$, $R^4$, X, n and the carbon-carbon bond between 3- and 4-positions in the carbostyril skeleton are the same as defined above; $X^3$ is a halogen atom; Z is a group of

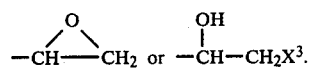

In the reaction process formula-6, the reaction of a compound represented by the general formula (8) with an epihalogenohydrin represented by the general formula (11) is carried out in the presence of a suitable basic compound, such as an inorganic basic compound, for example sodium hydroxide, potassium hydroxide, sodium carbonate, potassium carbonate, sodium ethoxide, sodium hydride, sodium metal, potassium metal, sodium amide or the like; or an organic basic compound, for example, piperidine, pyridine, triethylamine or the like; in the absence or presence of a suitable inert solvent as mentioned above, for example a lower alcohol, a ketone, an ether, an aromatic hydrocarbon, water or the like. In this reaction, the ratio of the amount of a compound represented by the general formula (11) to the amount of a compound represented by the general formula (8) is usually in an equimolar or an excess amount, preferably from an equimolar to 5–10 times the molar quantity of the latter. The reaction can be carried out at a temperature ranging from 0° to 150° C., preferably at 50° to 100° C. In the above-mentioned reaction, an epihalogenohydrin represented by the general formula (8) is reacted with the hydroxyl group in the compound represented by the general formula (11) to give (2,3-epoxy)propoxy group or 3-halogeno-2-hydroxypropoxy group to the latter. Generally, the reaction product is obtained as in the form of a mixture thereof.

The thus obtained reaction product can be used as it is, as in the form of mixture, without being purified to separate the respective ingredients of the mixture, to react with a piperidine derivative represented by the general formula (3). Alternatively, the reaction product is purified by applying a common. purification method, for example fractional recrystallization method, column chromatography method or the like, to separate the compound having 2,3-epoxypropoxy group and the compound having 3-halogeno-2-hydroxypropoxy group respectively; then each of the separated compounds can be reacted with a piperidine derivative represented by the general formula (3).

The reaction of a compound represented by the general formula (12) with a compound represented by the general formula (3) is carried out in the absence or presence of a suitable inert solvent at a temperature ranging from room temperature to about 200° C., preferably at a temperature from 60° to 120° C. and the reaction is completed within usually several hours to 24 hours.

In this reaction, as to solvent, there is not any specific restriction thereto and any solvent which may not give any adverse effect to the reaction can be used. The examples are the above-mentioned ethers, aromatic hydrocarbons, lower alcohols, dimethylformamide, dimethylsulfoxide or the like.

Further, in the reaction, if necessary, a usual basic compound can be added to the reaction system.

As to the basic compound, an inorganic basic compound such as potassium carbonate, sodium carbonate, sodium hydroxide, sodium hydrogencarbonate, sodium amide, sodium hydride or the like; an organic tertiary amine such as triethylamine, tripropylamine, pyridine, quinoline or the like can be exemplified.

The ratio of the amount of a compound represented by the general formula (3) to the amount of a compound represented by the general formula (12) is usually in an equimolar to an excess amount, preferably from an equimolar to 5 times the molar quantity, most preferably, from an equimolar to 1.2 times the molar quantity of the latter.

Among the present carbostyril derivative represent by the general formula (1), a compound in which $R^1$ is other than a hydrogen atom can be prepared from a compound in which $R^1$ is a hydrogen atom, as the starting material by a method as shown in reaction process formula-7 as follows:

REACTION PROCESS FORMULA-7

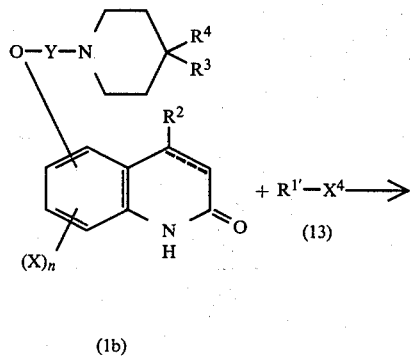

wherein $R^2$, $R^3$, $R^4$, X, Y, n and the carbon-carbon bond between 3- and 4-positions in the carbostyril skeleton are the same as defined above; $X^4$ is a halogen atom; $R^{1'}$ is a lower alkenyl group, a lower alkynyl group or a lower alkyl group which may have phenyl group(s) as the substituted group(s).

The reaction conditions in reaction process formula-7 mentioned above are similar to those used in the reaction of a compound represented by the general formulas (4), (6) or (8) wherein $R^1$ is a hydrogen, with a halide compound, except that a compound represented by the general formula (13) is used in an amount of from an equimolar to about 3 times the molar quantity, preferably an equimolar quantity of a compound represented by the general formula (1b).

Further, among the present carbostyril derivative represented by the general formula (1), the compound in which the carbon-carbon bond between 3- and 4-positions in the carbostyril skeleton is a double bond can be obtained by dehydrogenating a compound wherein the corresponding carbon-carbon bond between 3- and 4-positions in the carbostyril skeleton is a single bond. Alternatively, a carbostyril derivative represented by the general formula (1) wherein the carbon-carbon bond between 3- and 4-positions in the carbostyril skeleton is a single bond can be obtained by catalytically reducing a compound wherein the corresponding carbon-carbon bond between 3- and 4-positions in the carbostyril skeleton is a double bond. However, in the latter case, a compound having halogen atom(s), lower alkenyl group(s) or lower alkynyl group(s) as the substituted group(s) are not suitable to apply such catalytic reduction.

In addition to the above, the present carbostyril derivative represented by the general formula (1d) can be prepared by a method as shown in reaction process formula-8 as follows:

REACTION PROCESS FORMULA-8

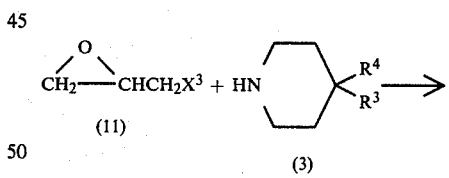

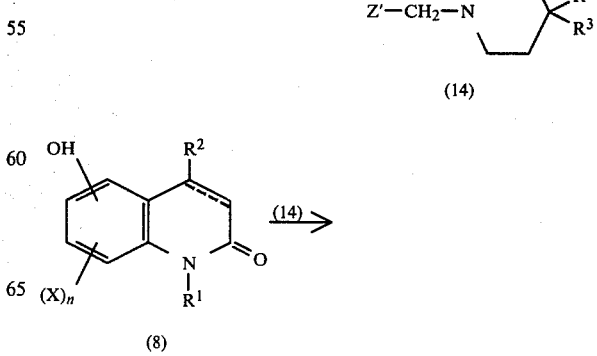

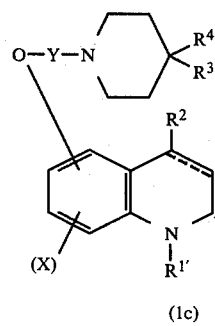

-continued

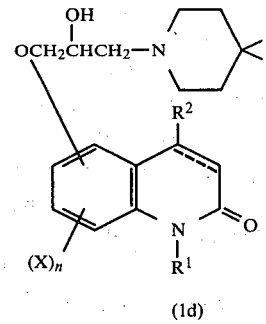

(1d)

wherein $R^1$, $R^2$, $R^3$, $R^4$, $X^3$, n and the carbon-carbon bond between 3- and 4-positions in the carbostyril skeleton are the same as defined above; Z' is a group of the formula

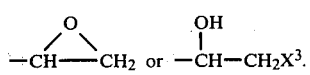

In reaction process formula-8, the reaction of a compound represented by the general formula (8) with a compound represented by the general formula (14) can be carried out under conditions similar to those used in the reaction of a compound represented by the general formula (12) with a compound represented by the general formula (3) in the above-mentioned reaction process formula-6. Further, the reaction of a compound represented by the general formula (3) with a compound represented by the general formula (11) can also be carried out under condition similar to those used in the reaction of a compound represented by the general formula (8) with a compound represented by the general formula (11).

Thus prepared carbostyril derivatives of the present invention can easily be converted into their acid-addition salts by reacting with pharmaceutically acceptable acids. The present invention includes such acid-addition salts. Examples of such acids include inorganic acids such as hydrochloric acid, sulfuric acid, phosphoric acid, hydrobromic acid and the like; organic acids such as acetic acid, oxalic acid, succinic acid, maleic acid, fumaric acid, malic acid, tartaric acid, citric acid, malonic acid, methansulfonic acid, benzoic acid and the like.

Among the present carbostyril derivatives, compounds wherein the carbon-carbon bond between 3- and 4-positions in the carbostyril skeleton is a double bond are easily form their salts by reacting basic compounds, such as metal oxides, for example potassium hydroxide, sodium hydroxide, calcium hydroxide or the like.

The present carbostyril derivative can form a quaternary salt by reacting the nitrogen atom in the piperidine ring with a halogenized lower alkyl as shown in reaction process formula-9 as follows:

REACTION PROCESS FORMULA-9

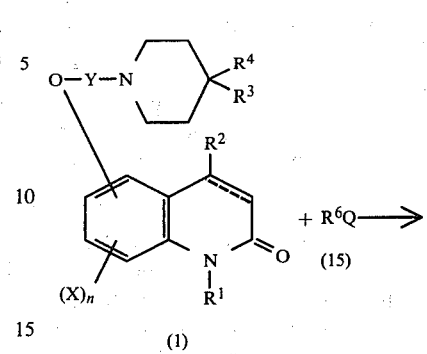

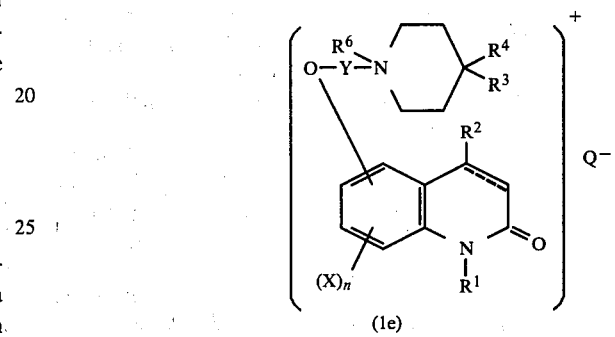

wherein $R^1$, $R^2$, $R^3$, $R^4$, Y, n and the carbon-carbon bond between 3- and 4-positions in the carbostyril skeleton are the same as defined above; $R^6$ is a lower alkyl group; Q is a halogen atom.

The reaction can advantageously be carried out in an inert solvent. As to the solvent, a lower alcohol such as methanol, ethanol, propanol or the like, an aromatic hydrocarbon such as benzene, toluene, xylene or the like, an ether such as tetrahydrofuran, dioxane or the like, chloroform, trichloroethylene, dimethylformamide (DMF), dimethylsulfoxide (DMSO), hexamethylphosphoryl triamide or the like can be exemplified.

The ratio of the amount of a compound represented by the general formula (15) to the amount of a compound represented by the general formula (1) is usually at least an equimolar quantity, preferably from an equimolar to 5 times the molar quantity of the latter. The reaction is usually carried out at a temperature ranging from 0° to about 200° C., preferably at a temperature ranging from a room temperature to 80° C., and the reaction is completed within a period of 1 to about 8 hours.

Among the present compounds represented by the general formula (1e) prepared by a method of reaction process formula-9, in case that Q is a halogen atom having the atomic number greater than that of chlorine atom, said compound can be converted into another compound wherein Q is chlorine atom, by reacting said compound with silver chloride. Similarly, in case that Q is a halogen atom having the atomic number greater than that of bromine atom, then said compound can be converted into another compound wherein Q is bromine atom, by reacting said compound with silver bromide. Such conversion reaction of the halogen atom can advantageously be carried out in the presence of a solvent such as the above-mentioned lower alcohol, dimethylformamide, dimethylsulfoxide or water. The ratio of the amount of the silver halogenide to the amount of the starting material is at least an equimolar quantity, preferably from an equimolar to 6 times the molar quantity of the latter. The reaction can be carried out at a temperature ranging from 0° to about 80° C., preferably at a temperature ranging from room temperature to 50° C., and the reaction is completed within a period of 5 to about 24 hours.

The desired compounds as prepared by the procedures in the above-mentioned various reaction process formulas can easily be isolated and purified by the usual separation means such as solvent extraction, dilution, recrystallization, column chromatography, preparative thin-layer chromatography.

Compounds of the present invention also include their optical isomers.

As for antihistaminic agents compounds of the general formula (1) can be used in the form of pharamaceutical compositions together with usual pharmaceutically acceptable carriers. The examples of the carriers which are used depending on the desired form of pharmaceutical composition include diluents or excipients such as fillers, diluents, binders, wetting agents, disintegrators, surface-active agents, lubricants.

No particular restriction is made to the administration unit forms and the compounds can be selected in any desired unit form as antihistaminic agents and typical unit form including tablets, pills, powders, liquors, suspensions, emulsions, granules, capsules, suppositories, injections (solutions and suspensions) and ointments. For the purpose of to shape in the form of tablets, carriers which are widely used in this field can also be used, for example excipients such as lactose, sucrose, sodium chloride, solution of glucose, urea, starch, calcium carbonate, caolin, crystalline cellulose, silicic acid; binding agents such as water, ethanol, propanol, simple syrup, glucose, starch solution, gelatin solution, carboxymethyl cellulose, shelac, methyl cellulose, calcium phosphate and polyvinylpyrrolidone; desintegrators such as dried starch, sodium alginate, agar-agar powder, laminalia powder, sodium hydrogencarbonate, calcium carbonate, Tweens, sodium laurylsulfate, monoglyceride of stearic acid, starch, lactose; desintegration inhibitor such as sucrose, stearin, coconut butter, hydrogenated oil; absorption accelarator such as quaternary ammonium base; sodium laurylsulfate; wetting agent such as glycerin or starch; adsorbing agents such as starch, lactose, caoline, bentonite, colloidal silicic acid; labricants such as purified talc, steraric acid salt, boric acid powder, Macrogol, solid polyethylene glycol. In case of tablets, they can be further coated with the usual coating materials to make sugar coated tablets, gelatin film coated tablets, tablets coated with enteric coatings, tablets coated with films or double layered tablets and multi-layered tablets.

For the purpose of to shape in the form of pills, carriers which are known and widely used in this field can also be used, for example, excipients such as glucose, lactose, starch, coconut butter, hydrogenated vegetable oils, caolin and talc; binders such as powdered Gummi Arabicum, powdered Tragacanth, gelatin and ethanol; desintegrators such laminaria and agar-agar are included.

For the purpose of to shape in the form of suppositories, carriers which are known and widely used in this field can also be used, for example, polyethylene glycols, coconut butter, higher alcohols, esters of higher alcohols, gelatin and semi-synthesized glycerids are included.

For the purpose of to make in the form of injection preparations, solutions and suspensions are sterilized and are preferably isotonic to blood. In making injection preparations, all carriers which are commonly used in this field can also be used, for example, water, ethyl alcohol, propylene glycol, ethoxylated isostearyl alcohol, polyoxylated isostearyl alcohol, polyoxyethylene sorbitol, sorbitane esters are included. In these instances, adequate amounts of sodium chloride, glucose or glycerin can be added to contain in the desired preparations for the purpose of to have them isotonic. Furthermore, the usual dissolving agents, buffers, analgesic agents, preservatives can be added as well as coloring materials, preservatives, perfumes, seasoning agents, sweetening agents and other medicines can also be added into the desired preparations if necessary.

For the purpose of to make preparations in the form of pastes and creams, diluents which are known and widely used in this field can also be used, for example, white vaseline, paraffin, glycerin, cellulose derivatives, polyethylene glycols, silicones and bentonite are included.

The amount of compounds of the general formula (1) or their acid addition salts to be contained in antihistaminic agents is not especially restricted and it can suitably be selected from wide range, but usually 1 to 70% by weight of the whole composition is preferable.

The above-mentioned antihistaminic agents and central nervous system controlling agents can be used in various forms depending on the purpose without any restriction. For example, tablets, pills, solutions, suspensions, emulsions, granules and capsules are administered orally; and injection preparations are administered intravenously singly or are mixed with injection transfusions such as glucose solutions and amino acid solutions; if necessary, the injection preparations are administered singly intramuscularly, intracutaneously, subcutaneously or intraperitoneally. Suppositories are administered into the rectum and ointments are administered by coating.

The dosage of the present antihistaminic agents is suitably selected according to the usage, purpose and conditions of symptoms and usually pharmaceutical composition containing 40 $\mu$g-2 mg/kg. day of the compound of the general formula (1) or its acid addition salt may be administered 3-4 times a day.

EXAMPLE OF PREPARATION OF TABLETS—1

By using the usual procedures, tablets having the following formulation were prepared.

| | |
|---|---|
| 1-Methyl-7-[3-(4-benzyl-1-piperidyl)propoxy]-3,4-dihydrocarbostyril monooxalate | 5 mg |
| Corn starch | 132 mg |
| Magnesium stearate | 18 mg |
| Lactose | 45 mg |
| Total | 200 mg |

EXAMPLE OF PREPARATION OF TABLETS—2

By using the usual procedures, tablets having the following formulation were prepared.

| | |
|---|---|
| 1-Methyl-5-[3-(4-benzyl-1-piperidyl)propoxy]-3,4-dihydrocarbostyril monooxalate | 5 mg |

-continued

| | |
|---|---|
| Corn starch | 132 mg |
| Magnesium stearate | 18 mg |
| Lactose | 45 mg |
| Total | 200 mg |

EXAMPLE OF PREPARATION OF TABLETS—3

By using the usual procedures, tablets having the following formulation were prepared.

| | |
|---|---|
| 7-[2-Hydroxy-3-(4-phenyl-1-piperidyl)propoxy]-3,4-dihydrocarbostyril | 10 mg |
| Corn starch | 132 mg |
| Magnesium stearate | 18 mg |
| Lactose | 45 mg |
| Total | 200 mg |

EXAMPLE OF PREPARATION OF TABLETS—4

By using the usual procedures, tablets having the following formulation were prepared.

| | |
|---|---|
| 4-Phenyl-1-[3-(2-oxo-1,2,3,4-tetrahydroquinolin-7-yloxy)propyl]-1-methylpiperidinium-chloride semihydrate | 5 mg |
| Corn starch | 132 mg |
| Magnesium stearate | 18 mg |
| Lactose | 45 mg |
| Total | 200 mg |

EXAMPLE OF PREPARATION OF TABLETS—5

By using the usual procedures, tablets having the following formulation were prepared.

| | |
|---|---|
| 5-[3-(4-Hydroxy-4-phenyl-1-piperidyl)propoxy]-3,4-di dihydrocarbostyril | 5 mg |
| Corn starch | 132 mg |
| Magnesium stearate | 18 mg |
| Lactose | 45 mg |
| Total | 200 mg |

PHARMACOLOGICAL TEST—1

Antihistaminic activity test

As to the test method for determining antihistaminic activity of a compound in vitro, a method of using an enucleated ileum of a guinea pig is generally accepted. Pharmacological tests of the present compounds were conducted according to said method as follows:

A male guinea pig having 300 to 500 g body weight is killed by blood letting. An ileum having length of 15 cm being enucleated from the ileocecal region is dipped into Tyrode's solution (which is prepared from 8.0 g of NaCl, 0.2 g of KCl, 0.2 g of $CaCl_2$, 1.0 g of glucose, 1.0 g of $NaHCO_3$, 0.065 g of $NaHPO_4.2H_2O$ and 0.2135 g of $MgCl_2.6H_2O$ to make 1000 ml in total volume by adding water). Then the tissue of ileum is cut to a length of 2.5 to 3.0 cm and suspended in an organ bath filled with 30 ml of Tyrode's solution. The organ bath is kept a temperature of 36° C. while blowing a mixed gas consisting of 5% of $CO_2$ and 95% of $O_2$ into the bath. 10 Minutes after the blowing, $10^{-6}$M of histamine is added to the bath to examine the sensitivity of the tissue and a reaction curve (control) with respect to the dosage of histamine is obtained. After the dosage of histamine-reaction curve (control) become constant $10^{-6}$g/ml of a compound to be tested is added to the bath and further histamine is added 5 minutes later to obtain dosage-reaction curve. Retraction of the ileum is recorded on a pen-recorder through an isotonic transducer (TD-112S manufactured by Nihon Koden). Antihistaminic activity of the test compound is determined as $pA_2$ value by "Van Rossam" method (J. M. Van Rossam: Arch. Inst. Pharmacodyn., ;b 143, 299 (1963)) in terms of that the maximum retraction of ileum caused by histamine shown in the control curve is 100%. The results are shown in Table 1.

| Compounds tested [Compounds of the present invention (Nos. 1–15)] | |
|---|---|
| Compound No. | Name of compound |
| 1. | 5-[3-(4-Benzyl-1-piperidyl)propoxy]-3,4-dihydrocarbostyril |
| 2. | 1-Methyl-7-[3-(4-benzyl-1-piperidyl)propoxy]-3,4-dihydrocarbostyril monooxalate |
| 3. | 1-Propargyl-5-[3-(4-benzyl-1-piperidyl)propoxy]-3,4-dihydrocarbostyril monohydrochloride |
| 4. | 1-Methyl-5-[3-(4-benzyl-1-piperidyl)propoxy]-3,4-dihydrocarbostyril monohydrochloride |
| 5. | 4-Methyl-7-[3-(4-benzyl-1-piperidyl)propoxy]-carbostyril |
| 6. | 1-Allyl-5-[2-hydroxy-(4-benzyl-1-piperidyl)-propoxy]-3,4-dihydrocarbostyril monooxalate |
| 7. | 1-Ethyl-5-[2-hydroxy-3-(4-benzyl-1-piperidyl)-propoxy]-3,4-dihydrocarbostyril monooxalate |
| 8. | 8-Bromo-5-[2-hydroxy-3-(4-benzyl-1-piperidyl)-propoxy]-3,4-dihydrocarbostyril |
| 9. | 7-[2-Hydroxy-3-(4-phenyl-1-piperidyl)propoxy]-3,4-dihydrocarbostyril |
| 10. | 1-Methyl-5-[2-hydroxy-3-(4-benzyl-1-piperidyl)-propoxy]-3,4-dihydrocarbostyril monooxalate |
| 11. | 4-Phenyl-1-[2-hydroxy-3-(2-oxo-1,2,3,4-tetrahydroquinolin-5-yloxy)propyl]-1-methyl-piperidium iodide |
| 12. | 1-Benzyl-5-[2-hydroxy-(4-benzyl-1-piperidyl)-propoxy]-3,4-dihydrocarbostyril monooxalate |
| 13. | 4-Phenyl-7-[3-(4-phenyl-1-piperidyl)propoxy]-carbostyril monohydrochoride |
| 14. | 5-{3-[4-(4-Hydroxy-4-phenyl)-1-piperidyl]}-3,4-dihydrocarbostyril |
| 15. | 7-{3-[4-(4-Acetyl-4-phenyl)-1-piperidyl]}-3,4-dihydrocarbostyril |

| [Comparative compounds A and B] | |
|---|---|
| A. | Diphenhydramine hydrochloride |
| B. | Chlorpheniramine maleate |

| [Reference compounds C to T] | |
|---|---|
| C. | 1,4-Dimethyl-7-{3-[4-(4-chlorobenzyl)-1-piperazin-1-yl]propoxy}-2-oxo-1,2-dihydroquinoline |
| D. | 1,4-Dimethyl-6-{3-[4-(4-chlorobenzyl-piperazin-1-yl]propoxy}-2-oxo-1,2-dihydroquinoline |
| E. | 4-Methyl-7-[3-(4-benzyl-piperazin-1-yl)-propoxy]-2-oxo-1,2-dihydroquinoline |
| F. | 8-(4-Phenyl-1-piperazinylpropoxy)carbostyril |
| G. | 7-(4-Phenyl-1-piperazinylpropoxy)carbostyril |
| H. | 4-Methyl-6-(4-phenyl-1-piperazinylpropoxy)-carbostyril |
| I. | 7-[4-β-Chlorophenyl)-1-piperazinylpropoxy]-carbostyril |
| J. | 4-Methyl-7-[4-chlorobenzyl)-1-piperazinyl-propoxy]carbostyril |

-continued

[Reference compounds C to T]

K. 8-Chloro-6-(1-hydroxy-2-tert-butylamino-ethyl)-3,4-dihydrocarbostyril monohydrochloride
L. 8-Chloro-6-[α-(β-3,4-dimethoxyphenethyl-amino)propionyl]-3,4-dihydrocarbostyril monohydrochloride
M. 8-Chloro-6-[1-hydroxy-2-(4-phenyl-1-piperazinyl)propyl]-3,4-dihydrocarbostyril monohydrochloride
N. 8-Chloro-6-[α-(4-phenyl)-1-piperazinyl)-propionyl]-3,4-dihydrocarbostyril hydrochloride
O. 8-Chloro-6-[1-hydroxy-2-(β-3,4-dimethoxy-phenethylamino)propyl]-3,4-dihydrocarbostyril hydrochloride
P. 8-Acetyoxy-5-{2-hydroxy-3-[4-(2-chloro-phenyl)-1-piperazinyl]propoxy}-3,4-dihydrocarbostyril hydrochloride
Q. 8-(2-Propionyloxy)-5-[2-hydroxy-3-(4-phenyl-1-piperazinyl)propoxy]-3,4-dihydrocarbostyril hydrochloride
R. Benzyloxy-5-{2-hydroxy-3-[4-(4-methoxy-phenyl)-1-piperazinyl]propoxy}-3,4-dihydrocarbostyril hydrochloride
S. 5-{2-Hydroxy-3-[4-(4-methoxyphenyl)-1-piperazinyl]propoxy}-8-ureido-3,4-dihydrocarbostyril hydrochloride
T. 8-Methanesulfonylamino-5-{2-hydroxy-3-[4-(2-methylphenyl)-1-piperazinyl]propoxy}-3,4-dihydrocarbostyril The results are show in Table 1.

TABLE 1

| Compound No. | pA$_2$ |
|---|---|
| [Compounds of the present invention] | |
| 1 | 9.52 |
| 2 | 10.70 |
| 3 | 9.73 |
| 4 | 11.00 |
| 5 | 9.59 |
| 6 | 9.54 |
| 7 | 9.65 |
| 8 | 8.39 |
| 9 | 9.89 |
| 10 | 9.62 |
| 11 | 8.23 |
| 12 | 10.70 |
| 13 | 9.73 |
| 14 | 9.30 |
| 15 | 9.92 |
| [Comparative and reference compounds] | |
| A | 8.15 |
| B | 9.00 |
| F | 8.58 |
| G | 9.53 |
| H | 9.57 |
| J | 9.13 |
| K | 4.32 |
| L | 5.32 |
| M | 5.19 |
| N | 6.21 |
| O | 5.83 |
| P | 7.62 |
| Q | 8.65 |
| R | 9.57 |
| S | 7.97 |
| T | 7.80 |

PHARAMACOLOGICAL TEST—2

Acute toxicity test

Each of the compounds of the present invention was orally administered to male rats to determine the acute toxicity. The results are shown in Table 2.

TABLE 2

Compounds tested

| Compound No. | Acute toxicity LD$_{50}$ mg/kg) |
|---|---|
| 1 | >1,000 |
| 2 | >1,000 |
| 3 | >1,000 |
| 4 | >1,000 |
| 5 | >1,000 |
| 6 | >1,000 |
| 7 | >1,000 |
| 8 | >1,000 |
| 9 | >1,000 |
| 10 | >1,000 |
| 11 | >1,000 |
| 12 | >1,000 |
| 13 | >1,000 |
| 14 | >1,000 |
| 15 | >1,000 |

PHARMACOLOGICAL TEST—3

Halothane anesthesia increasing activity

Male mice of ddy-strain having about 20 g body weight were used. One test group consists of 10 mice. An aqueous Gummi Arabicum suspension of test compound (80 mg of a compound to be tested and 1 g of Gummi Arabicum/100 ml of physiological NaCl solution) was administered orally to each mouse at the dosage of 32 mg of test compound/kg body. One hour after the administration, each mouse was placed in gas respiration chamber (13×13×24 cm) and oxygen gas containing 4% of Halothane [2-bromo-2-chloro-1,1,1-trifluoroethane] was blown into the chamber at the velocity of 2 l/min for 3 minutes. A mouse anaesthetized was taken out from the chamber and the time between the introduction of anesthesia to waking was measured by righting reflex as the index. To mice of control group, 1% Gummi Arabicum aqueous physiological solution was orally administered at the dosage of 0.1 ml/kg body. (Reference: M. J. Turnbull and J. W. Watkins: Br. J. Pharmacol., 58, 27–35 (1976))

The results are shown in Table 3.

TABLE 3

| Compound No. | Time (minutes) |
|---|---|
| 1 | 4.7 |
| 2 | 4.9 |
| 3 | 5.1 |
| 4 | 4.2 |
| 5 | 4.6 |
| 6 | 5.6 |
| 7 | 4.2 |
| 8 | 5.5 |
| 9 | 4.1 |
| 10 | 4.8 |
| 11 | 5.2 |
| 12 | 4.2 |
| 13 | 5.6 |
| 14 | 5.1 |
| 15 | 4.7 |
| P | 8.9 |
| Q | 8.7 |
| S | 9.1 |
| T | 8.9 |
| F | 9.5 |
| G | 28.7 |
| I | 32.7 |
| J | 8.5 |
| Saline (control) | 4.2 |

PHARMACOLOGICAL TEST—4

Local anesthesia activity test

Guinea pig having about 300 to 350 g of body weight were used as the test animals. Three (3) drops of 0.1%-test compound dissolved in physiological saline solution were administered through ¼-sized injection needle on the surface of conjuctiva of the test animal. After the administration of the test solution, the conjunctiva of the animal was stimulated ten times in every 5 minutes by a stylet (mandrine) or ¼-sized injection needle, the stimulations were repeated 6 times within 30 minutes, thus 60 stimulations were given to the conjunctiva of the animal. The number of disappearing of eye-closing-reflexes, during 30 minutes after the administration of the test solution was counted as to the effectiveness of the local anesthesia activity. In this test, four (4) guinea pigs were used as one test group, and the test solution containing 0.1% of the test compound was applied to one test group, and physiological saline solution was, on the other hand, applied to another test group of the guinea pigs as the control.

The results are shown in Table 4.

TABLE 4

| Compound tested | Number of eye-closing reflex |
|---|---|
| [Compound of the present invention] | |
| 1 | 55.1 |
| 2 | 58.0 |
| 9 | 29.2 |
| 10 | 37.3 |
| 11 | 27.6 |
| 13 | 28.0 |
| 15 | 35.5 |
| [Reference compounds] | |
| C | 2.8 |
| D | 3.8 |
| E | 5.2 |
| [Control] | |
| Saline solution | 0 |

As can be seen from Table 1, compounds of the present invention are more effective in antihistaminic activity than compounds of Japanese Patent Kokai No. 54-16478/1979 (K–O) as 2 or more higher value differences in pA$_2$, and have about same antihistaminic activity as compared with compounds of Japanese Patent Kokai No. 55-89221/1980 (P–R), compounds of Japanese Patent Kokai No. 55-89222/1980 (S, T) and compounds of Japanese Patent Kokai No. 55-2693/1980 (F, G, H, J).

However, compounds of the present invention have almost the same activity in Halothane anesthesia increasing activity as compared with physiological saline solution, thus compounds of the present invention have very weak Halothane anesthesia increasing activity or have no such activity.

On the other hand, compounds of Japanese Patent Kokai No. 55-89221/1980 (P, Q), compounds of Japanese Patent Kokai No. 55-89222/1980 (S, T) and Japanese Patent Kokai No. 55-2693/1980 (F, G, I, J) have a different Halothane anesthesia increasing activity as compared with control (physiological saline solution).

Further, compounds of the present invention have strong local anesthesia activity as compared with that of compound of Japanese Patent Kokai No. 55-2693/1980 (C to E). Compound of the present invention can be used for controlling excretion of pituita in common cold, and for controlling prickling of eczema. In controlling prickling of eczema, it is advantageous that such controlling agents have local anesthesia activity in certain extent.

As explained above, compounds of the present invention have weak central nervous controlling effect as the side-effect, and have effective local anesthesia activity. Thus compounds of the present invention are useful antihistaminic agents.

The present invention will be illustrated more specifically by way of the following examples, in which the preparation of the compounds to be used for the starting materials will be shown as Reference examples and the preparation of the objective compounds will be shown as Examples.

REFERENCE EXAMPLE 1

20.5 Grams of 5-acetyloxy-3,4-dihydrocarbostyril was dissolved in 200 ml of acetic acid, into this solution, 16 g of bromine dissolved in 60 ml of acetic acid was added dropwise under water-cooled condition with stirring for 30 minutes and the reaction was continued for 2 hours at the same temperature. Then 300 ml of water added to this reaction mixture and allowed to stand for 3 hours, and crystals formed in the mixture were obtained by filtration and recrystallized from methanol. 21 Grams of 8-bromo-5-acetyloxy-3,4-dihydrocarbostyril was obtained as in the form of colorless needle-like crystals. Melting point: 237°–239° C.

Then 21 g of thus obtained 8-bromo-5-acetyloxy-3,4-dihydrocarbostyril was dispersed in 150 ml of 8N-hydrochloric acid and was heated under refluxing condition for 3 hours. After the reaction mixture was cooled, the insoluble matters were obtained by filtration, washed with water, dried and recrystallized from methanol-water. 14 Grams of 8-bromo-5-hydroxy-3,4-dihydrocarbostyril was obtained as in the form of colorless needle-like crystals. Melting point: 212°–213° C.

REFERENCE EXAMPLE 2

35.4 Grams of 7-methoxy-3,4-dihydrocarbostyril was dissolved in 300 ml of acetic acid and under ice-cooled condition with stirring 27 g of sulfuryl chloride dissolved in 100 ml of acetic acid was added dropwise, then the reaction mixture was allowed to stand overnight. The reaction mixture was poured into 1 liter of ice water and the precipitates were obtained by filtration, washed with water, dried and recrystallized from methanol. 30 Grams of 6-chloro-7-methoxy-3,4-dihydrocarbostyril having the melting point of 212° C. was obtained as in the form of colorless needle-like crystals.

30 Grams of thus obtained 6-chloro-7-methoxy-3,4-dihydrocarbostyril was dispersed in 300 ml of 47% aqueous solution of hydrobromic acid and heated under refluxing condition for 4 hours. After the reaction mixture was cooled, the insoluble matters formed were obtained by filtration, washed with water, dried and recrystallized from methanol-chloroform. 25 Grams of 6-chloro-7-hydroxy-3,4-dihydrocarbostyril having the melting point of 264°–266° C. was obtained as in the form of colorless needle-like crystals.

REFERENCE EXAMPLE 3

16.4 Grams of 5-hydroxy-3,4-dihydrocarbostyril was dissolved in 300 ml of acetic acid, and under stirring condition at a room temperature 80 ml of acetic acid containing 14 g chlorine was added dropwise and the reaction was continued for 3 hours under stirring. The reaction mixture was poured into 500 ml of water and allowed to stand for 1 hour. The precipitates thus formed were obtained by filtration, and washed with water, dried and recrystallized from methanol. 16 Grams of 6,8-dichloro-5-hydroxy-3,4-dihydrocarbostyril was obtained as in the form of colorless needle-like crystals. Melting point: 259°–260° C.

REFERENCE EXAMPLE 4

20.0 Grams of 8-bromo-5-hydroxy-3,4-dihydrocarbostyril and 18 g of potassium carbonate were dispersed in 160 ml of isopropanol, then 40 ml of epichlorohydrin was added thereinto and reacted at 80° C. for 6 hours. The reaction mixture was concentrated under a reduced pressure and to the residue thus obtained was added 100 ml of 2N-sodium hydroxide and stirred well. The insoluble matters formed were obtained by filtration and washed with water and dried to obtain crude crystals. Recrystallization of the crude crystal from methanol to obtain 18.5 g of 8-bromo-5-(2,3-epoxypropoxy)-3,4-dihydrocarbostyril as in the form of colorless needle-like crystals. Melting point: 220°–220° C.

REFERENCE EXAMPLE 5

16.4 Grams of 5-hydroxy-3,4-dihydrocarbostyril and 3.7 g of sodium hydroxide were added into 100 ml of methanol and stirred at 40°–50° C. for 3 hours, then 150 ml of epichlorohydrin was added thereto and heated under refluxing condition for 5 hours. The reaction mixture was concentrated under a reduced pressure to dryness and the residue thus obtained was recrystallized from methanol-water (1:1) to obtain 18.5 g of 5-(2,3-epoxypropoxy)-3,4-dihydrocarbostyril having the melting of 172°–173° C. as in the form of coloress amorphous crystals.

REFERENCE EXAMPLE 6

16.3 Grams of 5-hydroxy-3,4-dihydrocarbostyril and 9 g of potassium hydroxide were mixed with 150 ml of isopropanol and stirred at 70°–80° C. for 30 minutes. Next, 25 g of 1,3-bromochloropropane was added thereinto and heated under refluxing condition for 6 hours. After the reaction was completed, the reaction mixture was poured into 200 ml of 2N-sodium hydroxide aqueous solution and the insoluble matters thus formed were obtained by filtration, washed with water and dried. Crude crystals thus obtained were recrystallized from ethanol to obtain 18.5 g of 5-(3-chloropropoxy)-3,4-dihydrocarbostyril as in the form of colorless needle-like crystals. Melting point: 176°–178° C.

REFERENCE EXAMPLE 7

24 Grams of 4-phenylpiperidine, 24 g of 1-chloro-3-bromopropane and 15 g of triethylamine were mixed with 100 ml of dimethylformamide and stirred at 50°–60° C. for 1 hour. The reaction mixture was poured into 200 ml of saturated sodium chloride aqueous-solution and the organic layer was extracted with chloroform. Then the chloroform layers was washed with water, dried and the chloroform was removed by distillation. The residue thus obtained was purified by a silica-gel column chromatography (to obtain only the main product at the upper-most portion in the column). 15.3 Grams of 1-chloro-3-(4-phenylpiperidinyl)propane was obtained as in the form of colorless oily substance. Then this oily substance was distilled under a reduced pressure to obtain 11 g of a fraction of distillate having the boiling point of 112°–115° C. (0.1 mmHg). A part of this distillate was made as in the form of hydrochloride and recrystallized from ethanol to obtain 1-chloro-3-(4-phenyl-1-piperidyl)propane monohydrochloride having the melting point of 167°–169° C. as in the form of colorless needle-like crystals.

REFERENCE EXAMPLE 8

By a method similar to that described in Reference Example 7, 1-chloro-2-methyl-3-(4-phenyl-1-piperidyl)propane was obtained as in the form of colorless oily substance. Boiling point: 114°–116° C./0.1 mmHg.

REFERENCE EXAMPLE 9

16.0 Grams of 4-hydroxy-4-phenylpiperidine, 24 g of 1-chloro-3-bromopropane and 15 g of triethylamine were mixed with 100 ml of dimethylformamide and stirred at 50°–60° C. for 1 hour. The reaction mixture was poured into 200 ml of saturated sodium chloride aqueous solution and the organic layer was extracted with chloroform, then the chloroform layer was washed with water, dried and the chloroform was removed by distillation. The residue thus obtained was purified by a silica-gel column chromatography (to obtain only the main product at the upper-most portion in the column). 14.3 Grams of 1-chloro-3-(4-hydroxy-4-phenyl-1-piperidyl)propane was obtained as in the form of colorless oily substance. Then this oily substance was distilled under a reduced pressure to obtain a fraction of distillate. The fraction of distillate was made as in the form of hydrochloride and recrystallized from ethanol to obtain 1-chloro-3-(4-hydroxy-4-phenyl-1-piperidyl)propane monohydrochloride having the melting point of 192°–195° C. as in the form of colorless needle-like crystals.

EXAMPLE 1

4.8 Grams of 5-(3-chloropropoxy)-3,4-dihydrocarbostyril and 4.2 g of 4-benzylpiperidine were mixed with 40 ml of toluene and the mixture was heated under refluxing condition for 24 hours. After cooling of the reaction mixture, the precipitates thus formed were obtained by filtration and washed with water, then recrystallized from ethanol to obtain 6.3 g (yield: 76%) of 5-[3-(4-benzyl-1-piperidyl)propoxy]-3,4-dihydrocarbostyril as in the form of colorless needle-like crystals. Melting point: 143°–145° C.

EXAMPLE 2

4.9 Grams of 1-methyl-7-(3-chloropropoxy)-3,4-dihydrocarbostyril, 4.2 g of 4-benzylpiperidine and 3 g of triethylamine were mixed with 60 ml of dimethylformamide. The mixture was heated at 70°–80° C. for 8 hours. After the reaction was completed, the reaction mixture was concentrated under a reduced pressure to dryness. To the residue thus obtained was added 5%-sodium hydrogencarbonate aqueous solution and extracted with chloroform. The chloroform layer was washed with water and dried, then chloroform was removed by distillation. The residue thus obtained was dissolved in 30 ml of acetone, and under stirring condition a 5%-oxalic acid acetone solution was added thereto to make pH 4.5 then was allowed to stand. Precipitates thus formed were obtained by filtration, washed with acetone, then recrystallized from ethanol-ether to obtain 7.9 g (yield: 86%) of 1-methyl-7-[3-(4-benzyl-1-piperidyl)propoxy]-3,4-dihydrocarbostyril monooxalate as in the form of colorless powder. Melting point: 175°–177° C.

By a method similar to that described in Example 2, there were obtained compounds of Examples 3–16 as follows:

EXAMPLE 3

1-Propargyl-5-[3-(4-benzyl-1-piperidyl)propoxy]-3,4-dihydrocarbostyril monohydrochloride monohydrate
Colorless needle-like crystals (from methanol-ether)
Melting point: 172° C. (decomposed)

EXAMPLE 4

1-Methyl-5-[3-(4-benzyl-1-piperidyl)propoxy]-3,4-dihydrocarbostyril monohydrochloride
Colorless needle-like crystals (from ethanol-ether)
Melting point: 130°–133° C.

EXAMPLE 5

1-Hexyl-7-[3-(4-phenyl-1-piperidyl)propoxy]-3,4-dihydrocarbostyril monooxalate
Colorless needle-like crystals (from isopropanol)
Melting point: 168°–170° C.

EXAMPLE 6

1-(3-Phenylpropyl)-7-[3-(4-phenyl-1-piperidyl)propoxy]-3,4-dihydrocarbostyril monooxalate
Colorless needle-like crystals (from methanol-water)
Melting point: 210°–213° C.

EXAMPLE 7

6,8-Dichloro-5-[2-methyl-3-(4-phenyl-1-piperidyl)propoxy]-3,4-dihydrocarbostyril
Colorless needle-like crystals (from ligroin)
Melting point: 125°–126° C.

EXAMPLE 8

5-[3-(4-Benzyl-1-piperidyl)propoxy]-3,4-dihydrocarbostyril monohydrochloride
Colorless needle-like crystals (from methanol)
Melting point: 213°–215° C.

EXAMPLE 9

5-[3-(4-Benzyl-1-piperidyl)propoxy]-3,4-dihydrocarbostyril
Colorless needle-like crystals (from lgroinbenzene)
Melting point: 143°–145° C.

EXAMPLE 10

7-[3-(4-Benzyl-1-piperidyl)propoxy]-3,4-dihydrocarbostyril monooxalate
Colorless prism-like crystals (from ethanol)
Melting point: 175°–177° C.

EXAMPLE 11

7-[3-(4-Phenyl-1-piperidyl)propoxy]-3,4-dihydrocarbostyril monohydrochloride
Yellowish needle-like crystals (from ethanol)
Melting point: 252°–254° C.

EXAMPLE 12

4-Methyl-7-[3-(4-benzyl-1-piperidyl)propoxy]-carbostyril monohydrochloride dihydrate
Colorless needle-like crystals (from ethanol)
Melting point: 241°–242° C.

EXAMPLE 13

5-[3-(4-Phenyl-1-piperidyl)propoxy]-3,4-dihydrocarbostyril monohydrochloride
Colorless needle-like crystals (from methanol)
Melting point: 200° C.

EXAMPLE 14

4-Methyl-6-{3-[4-(4-methylphenyl)-1-piperidyl]-propoxy}carbostyril monyhydrochloride
Colorless needle-like crystals (from methanol)
Melting point: 256°–259° C. (decomposed)

EXAMPLE 15

4-Methyl-6-{3-[4-(4-chlorophenyl)-1-piperidyl]-propoxy}carbostyril monohydrochloride
Colorless needle-like crystals (from methanol)
Melting point: 263°–265° C.

EXAMPLE 16

1-Isopentyl-6-{2-hydroxy-3-[4-(3,4,5-trimethoxyphenyl)-1-piperidyl]propoxy}-3,4-dihydrocarbostyril monooxalate
Colorless flake-like crystals (from ethanol)
Melting point: 199°–201° C.

EXAMPLE 17

2.7 Grams of 7-(5-bromopentoxy)-3,4-dihydrocarbostyril, 2.0 g of 4-benzylpiperidine and 1.5 g of triethylamine were mixed with 30 ml of dimethylformamide and the mixture was heated at 60°–70° C. for 6 hours. The reaction mixture was then concentrated under a reduced pressure to dryness, and to the residue thus obtained was added a 5%-sodium hydrogencarbonate aqueous solution and stirred. The insoluble matters thus formed were collected by filtration, washed with water and dried. Recrystallization from ligroin to obtain 3.6 g (yield: 88%) of 7-[5-(4-benzyl-1-piperidyl)pentoxy]-3,4-dihydrocarbostyril as in the form of colorless plate-like crystals. Melting point: 100°–102° C.

EXAMPLE 18

2.5 Grams of 4-methyl-6-(3-chloropropoxy)carbostyril, 1.8 g of sodium iodide were mixed with 50 ml of acetone and the mixture was stirred at 50° C. for 1 hour, then 50 ml of dimethylformamide was added and acetone was removed by distillation under a reduced pressure. To the residue thus obtained was added 1.5 g of triethylamine and 1.6 g of 4-benzylpiperidine and the mixture was heated at 70°–80° C. for 7 hours under stirring condition. The reaction mixture was then concentrated under a reduced pressure to dryness and to the residue thus obtained was added 60 ml of a 5%-sodium hydrogencarbonate aqueous solution and stirred to obtain the insoluble matters. The insoluble matters were collected by filtration, washed with water and then recrystallized from methanol to obtain 3.2 g (yield: 82%) of 4-methyl-6-[3-(4-benzyl-1-piperidyl)propoxy]-carbostyril as in the form of yellowish prism-like crystals. Melting point: 177°–178° C.

By a method similar to that described in Example 18, there were obtained compounds of Examples 19–24 as follows:

EXAMPLE 19

4-Methyl-7-[3-(4-benzyl-1-piperidyl)propoxy]-carbostyril
Colorless needle-like crystalls (from methanol)
Melting point: 183°–184° C.

EXAMPLE 20

4-Phenyl-7-[3-(4-phenyl-1-piperidyl)propoxy]-carbostyril monohydrochloride
Colorless needle-like crystals (from methanol-ether)
Melting point: 238°–241° C.

EXAMPLE 21

4-Methyl-6-[3-(4-benzyl-1-piperidyl)propoxy]-carbostyril
Yellow-brown prism-like crystals (from methanol)
Melting point: 177°–178° C.

EXAMPLE 22

4-Methyl-6-[3-(4-benzyl-1-piperidyl)propoxy]-carbostyril monohydrochloride
Colorless powdery crystals (from ethanol-acetone-ether)
Melting point: 217° C.

EXAMPLE 23

4-Methyl-6-{3-[4-(4-methylphenyl)-1-piperidyl]-propoxy}carbostyril monohydrochloride
Colorless needle-like crystals (from methanol)
Melting point: 256°–259° C. (decomposed)

EXAMPLE 24

4-Methyl-6-{3-[4-(4-chlorophenyl)-1-piperidyl]-propoxy}carbostyril monohydrochloride
Colorlelss needle-like crystals (from methanol)
Melting point: 263°–265° C.

EXAMPLE 25

2.6 Grams of 1-allyl-5-(2-hydroxy-3-chloropropoxy)-3,4-dihydrocarbostyril, 1.5 g of triethylamine and 2.0 g of 4-benzylpiperidine were mixed with 30 ml of dimethylformamide and the mixture was stirred at 80°–90° C. for 5 hours. The reaction mixture was poured into 80 ml of a 5%-sodium hydrogencarbonate aqueous solution and the organic layer was extracted with chloroform, and the chloroform layer was washed with water and dried. Then the chloroform was removed by distillation and the residue thus obtained was dissolved in 30 ml of acetone and further 5%-oxalic acid acetone solution was added to make the pH to 4.5 and the crystals formed were collected by filtration and washed with acetone. Recrystallization from ethanol to obtain 4.3 g (yield: 82%) of 1-allyl-5-[2-hydroxy-(4-benzyl-1-piperidyl)propoxy]-3,4-dihydrocarbostyril monooxalate as in the form of colorless needle-like crystals. Melting point: 178°–180° C.

By a method similar to that described in Example 25, there were obtained compounds of Examples 26–36 as follows:

EXAMPLE 26

1-Benzyl-5-[2-hydroxy-3-(4-benzyl-1-piperidyl)propoxy]-3,4-dihydrocarbostyril monooxalate
Colorless powdery crystals (from ethanol-ether)
Melting point: 213°–214° C. (decomposed)

EXAMPLE 27

1-Ethyl-5-[2-hydroxy-3-(4-benzyl-1-piperidyl)propoxy]-3,4-dihydrocarbostyril monooxalate
Colorless needle-like crystals (from ethanol)
Melting point: 164°–169° C.

EXAMPLE 28

8-Bromo-5-[2-hydroxy-3-(4-benzyl-1-piperidyl)propoxy]-3,4-dihydrocarbostyril
Colorless needle-like crystals (from ethanol)
Melting point: 165°–166° C.

EXAMPLE 29

5-[2-Hydroxy-3-(4-phenyl-1-piperidyl)propoxy]-3,4-dihydrocarbostyril
Colorless needle-like crystals (from ethanol)
Melting point: 207°–208° C.

EXAMPLE 30

6-[2-Hydroxy-3-(4-phenyl-1-piperidyl)propoxy]-3,4-dihydrocarbostyril
Colorless plate-like crystals (from ethanol)
Melting point: 170°–171° C.

EXAMPLE 31

7-[2-Hydroxy-3-(4-phenyl-1-piperidyl)propoxy]-3,4-dihydrocarbostyril
Colorless needle-like crystals (from isopropanol)
Melting point: 149°–150° C.

EXAMPLE 32

1-Allyl-5-[2-hydroxy-3-(4-phenyl-1-piperidyl)propoxy]-3,4-dihydrocarbostyril
Colorless needle-like crystals (from ligroin)
Melting point: 92° C.

EXAMPLE 33

1-Allyl-5-[2-hydroxy-3-(4-phenyl-1-piperidyl)propoxy]-3,4-dihydrocarbostyril monooxalate
Yellowish needle-like crystals (from methanol)
Melting point 208° C. (decomposed)

EXAMPLE 34

1-Methyl-5-[2-hydroxy-3-(4-benzyl-1-piperidyl)propoxy]-3,4-dihydrocarbostyril monooxalate
Colorless powdery crystals (from ethanol-ether
Melting point: 150°–152° C.

EXAMPLE 35

1-Benzyl-5-[2-hydroxy-3-(4-benzyl-1-piperidyl)propoxy]-3,4-dihydrocarbostyril
Colorless needle-like crystals (from ethanol
Melting point: 141°–143° C.

EXAMPLE 36

1-Isopentyl-6-{2-hydroxy-3-[4-(3,4,5-trimethoxyphenyl)-1-piperidyl]propoxy}-3,4-dihydrocarbostyril monooxalate
Colorless flake-like crystals (from ethanol)
Melting point: 199°–201° C.

EXAMPLE 37

2.4 Grams of 1-methyl-5-(2,3-epoxypropoxy)-3,4-dihydrocarbostyril and 2.0 g of 4-benzylpiperidine were mixed with 30 ml of methanol and the mixture was heated under refluxing condition for 3 hours. The reaction mixture was concentrated under a reduced pressure and the residue thus obtained was dissolved in 30 ml of acetone and a 5%-oxalic acid-acetone solution was added under stirring at a room temperature to adjust the pH to 4.5 and allowed to stand. The precipitates thus formed were collected by filtration, washed with acetone and recrystallized from ethanol-ether to obtain 3.9 g (yield: 78%) of 1-methyl-5-[2-hydroxy-3-(4-benzyl-1-piperidyl)propoxy]-3,4-dihydrocarbostyril monooxalate as in the form of colorless powder. Melting point: 150°–152° C.

By a method similar to that described in Example 37, there were obtained compounds of Examples 38–47 as follows:

EXAMPLE 38

6-[2-Hydroxy-3-(4-phenyl-1-piperidyl)propoxy]-3,4-dihydrocarbostryril
Colorless plate-like crystals (from ethanol)
Melting point: 170°–171° C.

EXAMPLE 39

1-Ethyl-5-[2-hydroxy-3-(4-benzyl-1-piperidyl)propoxy]-3,4-dihydrocarbostyril monooxalate
Colorless needle-like crystals (from ethanol)
Melting point: 164°–169° C.

EXAMPLE 40

8-Bromo-5-[2-hydroxy-3-(4-benzyl-1-piperidyl)propoxy]-3,4-dihydrocarbostyril
Colorless needle-like crystals (from ethanol)
Melting point: 165°–166° C.

EXAMPLE 41

7-[2-Hydroxy-3-(4-phenyl-1-piperidyl)propoxy]-3,4-dihydrocarbostyril
Colorless needle-like crystals (from isopropanol)
Melting point: 149°–150° C.

EXAMPLE 42

5-[2-Hydroxy-3-(4-phenyl-1-piperidyl)propoxy]-3,4-dihydrocarbostyril
Colorless needle-like crystals (from ethanol)
Melting point: 207°–208° C.

EXAMPLE 43

1-Benzyl-5-[2-hydroxy-3-(4-benzyl-1-piperidyl)propoxy]-3,4-dihydrocarbostyril
Colorless needle-like crystals (from ethanol)
Melting point: 141°–143° C.

EXAMPLE 44

1-Isopentyl-6-{2-hydroxy-3-[4-(3,4,5-trimethoxyphenyl)-1-piperidyl]propoxy}-3,4-dihydrocarbostyril monooxalate
Colorless flake-like crystals (from ethanol)
Melting point: 199°–201° C.

EXAMPLE 45

1-Methyl-5-[2-hydroxy-3-(4-benzyl-1-piperidyl)propoxy]-3,4-dihydrocarbostyril monooxalate
Colorless powdery crystals (from ethanol-ether)
Melting point: 150°–152° C.

EXAMPLE 46

1-Allyl-5-[2-hydroxy-3-(4-phenyl-1-piperidyl)propoxy]-3,4-dihydrocarbostyril
Colorless needle-like crystals (from ligroin)
Melting point: 92° C.

EXAMPLE 47

1-Allyl-5-[2-hydroxy-3-(4-phenyl-1-piperidyl)propoxy]-3,4-dihydrocarbostyril monooxalate
Yellowish needle-like crystals (from methanol)
Melting point: 208° C. (decomposed)

EXAMPLE 48

3.8 Grams of 5-[3-(4-benzyl-1-piperidyl)propoxy]-3,4-dihydrocarbostyril and 0.6 g of sodium hydride (50% in oil) were mixed in 60 ml of dimethylformamide under stirring for 1 hour, then 1.4 g of propargyl was added to the mixture and stirred at a room temperature for 2 hours. The reaction mixture was poured into 100 ml of saturated sodium chloride aqueous solution and the organic layer was extracted with chloroform. The chloroform layer was dried and the chloroform was removed by distillation. The residue thus obtained was recrystallized from ethanol-hydrochloric acid to obtain 4.1 g (yield: 87%) of 1-propargyl-5-[3-(4-benzyl-1-piperidyl)propoxy]-3,4-dihydrocarbostyril monohydrochloride monohydrate as in the form of colorless needle-like crystals. Melting point: 172° C. (decomposed).

By a method similar to that described in Example 48, there were obtained compounds of Examples 49–54 as follows:

EXAMPLE 49

1-Methyl-5-[3-(4-benzyl-1-piperidyl)propoxy]-3,4-dihydrocarbostyril monohydrochloride
Colorless needle-like crystals (from ethanol-ether)
Melting point: 130°–133° C.

EXAMPLE 50

1-n-Hexyl-7-[3-(4-phenyl-1-piperidyl)propoxy]-3,4-dihydrocarbostyril monooxalate
Colorless needle-like crystals (from isopropanol)
Melting point: 168°–170° C.

EXAMPLE 51

1-(3-Phenylpropyl)-7-[3-(4-phenyl-1-piperidyl)propoxy]-3,4-dihydrocarbostyril monooxalate
Colorless needle-like crystals (from methanol-water)
Melting point: 210°–213° C.

EXAMPLE 52

1-Methyl-7-[3-(4-benzyl-1-piperidyl)propoxy]-3,4-dihydrocarbostyril monooxalate
Colorless powdery substance (from ethanol-ether)
Melting point: 175°–177° C.

EXAMPLE 53

1-Benzyl-5-[2-hydroxy-3-(4-benzyl-1-piperidyl)propoxy]-3,4-dihydrocarbostyril
Colorless needle-like crystals (from ethanol)
Melting point: 141°–143° C.

EXAMPLE 54

1-Isopentyl-6-{2-hydroxy-3-[4-(3,4,5-trimethoxyphenyl)-1-piperidyl]propoxy}-3,4-dihydrocarbostyril monooxalate
Colorless flake-like crystals (from ethanol)
Melting point: 199°–201° C.

EXAMPLE 55

2.4 Grams of 7-hydroxy-4-phenylcarbostyril and 0.8 g of potassium hydroxide were mixed with 60 ml of methanol and concentrated under a reduced pressure to dryness. To the residue thus obtained was added 60 ml of dimethylformamide and well mixed, then 5 g of 1-(3-chloropropyl)-4-phenylpiperidine was added to the mixture and heated at 70°–80° C. for 8 hours under stirring condition. The reaction mixture was concentrated under a reduced pressure to dryness, and to the residue thus obtained was added 60 ml of 5% sodium hydrogencarbonate aqueous solution and extracted with chloroform. The chloroform layer was washed with water, dried and the chloroform was removed by distillation. To the residue thus obtained was added 30 ml of methanol and 5 ml of concentrated hydrochloric acid, and concentrated under a reduced pressure. The residue was crystallized with ethanol then recrystallized from methanol to obtain 2.8 g (58%) of 4-phenyl-7-[3-(4-phenyl-1-piperidyl)propoxy]carbostyril monohydrochloride as in the form of colorless needle-like crystals. Melting point: 238°–241° C.

By a method similar to that described in Example 55, there were obtained compounds of Examples 56–76 as follows:

EXAMPLE 56

1-Methyl-7-[3-(4-benzyl-1-piperidyl)propoxy]-3,4-dihydrocarbostyril monooxalate
Colorless powdery substance (from ethanol-ether)
Melting point: 175°–177° C.

EXAMPLE 57

1-Propargyl-5-[3-(4-benzyl-1-piperidyl)propoxy]-3,4-dihydrocarbostyril monohydrochloride monohydrate
Colorless neelde-like crystals (from methanolehter)
Melting point: 172° (decomposed)

EXAMPLE 58

1-Methyl-5-[3-(4-benzyl-1-piperidyl)propoxy]-3,4-dihydrocarbostyril monohydrochloride
Colorless needle-like crystals (from ethanol-ether)
Melting point: 130°–133° C.

EXAMPLE 59

1-Hexyl-7-[3-(4-phenyl-1-piperidyl)propoxy]-3,4-dihydrocarbostyril monooxalate
Colorless needle-like crystals (from isopropanol)
Melting point: 168°–170° C.

EXAMPLE 60

1-(3-Phenylpropyl)-7-[3-(4-phenyl-1-piperidyl)propoxy]-3,4-dihydrocarbostyril monooxalate
Colorless needle-like crystals (from methanol-water
Melting point: 210°–213° C.

EXAMPLE 61

1-Allyl-5-[2-hydroxy-(4-benzyl-1-piperidyl)propoxy]-3,4-dihydrocarbostyril monooxalate
Colorless needle-like crystals (from ethanol)
Melting point: 178°–180° C.

EXAMPLE 62

1-Methyl-5-[2-hydroxy-3-(4-benzyl-piperidyl)propoxy]-3,4-dihydrocarbostyril monooxalate
Colorless powdery crystals (from ethanol-ether)
Melting point: 150°–152° C.

EXAMPLE 63

1-Benzyl-5-[2-hydroxy-3-(4-benzyl-1-piperidyl)propoxy]-3,4-dihydrocarbostyril
Colorless needle-like crystals (from ethanol)
Melting point: 141°–143° C.

EXAMPLE 64

5-[3-(4-Benzyl-1-piperidyl)propoxy]-3,4-dihydrocarbostyril monohydrochloride
Colorless needle-like crystals (from methanol)
Melting point: 213°–215° C.

EXAMPLE 65

5-[3-(4-Benzyl-1-piperidyl)propoxy]-3,4-dihydrocarbostyril
Colorless needle-like crystal (from ligroinbenzene)
Melting point: 143°–145° C.

EXAMPLE 66

7-[3-(4-Benzyl-1-piperidyl)propoxy]-3,4-dihydrocarbostyril monooxalate
Colorless prism-like crystal (from ethanol)
Melting point: 175°–177° C.

EXAMPLE 67

1-Allyl-5-[2-hydroxy-3-(4-phenyl-1-piperidyl)propoxy]-3,4-dihydrocarbostyril
Colorless needle-like crystals (from ligroin)
Melting point: 92° C.

EXAMPLE 68

1-Allyl-5-[2-hydroxy-3-(4-phenyl-1-piperidyl)propoxy]-3,4-dihydrocarbostyril monooxalate
Yellowish needle-like crystals (from methanol)
Melting point: 208° C. (decomposed)

EXAMPLE 69

4-Methyl-6-[3-(4-benzyl-1-piperidyl)propoxy]carbostyril
Yellow-brown prism-like crystals (from methanol)
Melting point: 177°–178° C.

EXAMPLE 70

4-Methyl-6-[3-(4-benzyl-1-piperidyl)propoxy]carbostyril monohydrochloride
Colorless powdery crystals (from ethanolacetoneether)
Melting point: 217° C.

EXAMPLE 71

5-[3-(4-Phenyl-1-piperidyl)propoxy]carbostyril monohydrochloride
Colorless needle-like crystals (from methanol)
Melting point: 200° C.

EXAMPLE 72

7-[3-(4-Phenyl-1-piperidyl)propoxy]-3,4-dihydrocarbostyril monohydrochloride
Yellowish needle-like crystals (from ethanol)
Melting point: 252°–254° C.

EXAMPLE 73

4-Methyl-7-[3-(4-benzyl-1-piperidyl)propoxy]carbostyril monohydrochloride dihydrate
Colorless needle-like crystals (from ethanol)
Melting point: 241°–242° C.

EXAMPLE 74

4-Methyl-6-{3-[4-(4-methylphenyl)-1-piperidyl]propoxy}carbostyril monohydrochloride
Colorless needle-like crystals (from methanol)
Melting point: 256°–259° C. (decomposed)

EXAMPLE 75

4-Methyl-6-{3-[4-(4-chlorphenyl)-1-piperidyl]propoxy}carbostyril monohydrochloride
Colorless needle-like crystals (from methanol)
Melting point: 263°–265° C.

EXAMPLE 76

1-Isopentyl-6-{2-hydroxy-3-[4-(3,4,5-trimethoxyphenyl)-1-piperidyl]propoxy}-3,4-dihydrocarbostyril monooxalate
Colorless flake-like crystals (from ethanol)
Melting point: 199°–201° C.

EXAMPLE 77

2.4 Grams of 6,8-dichloro-5-hydroxy-3,4-dihydrocarbostyril and 0.8 g of granular potassium hydroxide were mixed with 60 ml of methanol and concentrated under a reduced pressure to dryness. To the residue thus obtained was added 60 ml of dimethylformamide and mixed well, then 5 g of 1-chloro-2-methyl-3-(4-phenyl-1-piperidyl)propane and heated at 70°–80° C. for 8 hours under stirring condition. The reaction mixture was concentrated under a reduced pressure to dryness, then 60 ml of 5% sodium hydrogencarbonate aqueous solution was added thereto and extracted with chloroform. The chloroform layer was washed with water and dried, then the chloroform was removed by distillation and thus obtained residue was purified by silica-gel column chromatography and recrystallized from ligroin to obtain 1.6 g (yield: 35%) of 6,8-dichloro-5-[2-methyl-3-(4-phenyl-1-piperidyl)propoxy]-3,4-dihydrocarbostyril as in the form of colorless needle-like crystals. Melting point 125°–126° C.

By a method similar to that described in Example 77 there were obtained compounds of Examples 78–82 as follows:

EXAMPLE 78

5-[3-(4-Benzyl-1-piperidyl)propoxy]-3,4-dihydrocarbostyril
Colorless needle-like crystals (from ethanol)
Melting point: 143°–145° C.

EXAMPLE 79

7-[5-(4-Benzyl-1-piperidyl)pentoxy]-3,4-dihydrocarbostyril
Colorless plate-like crystals (from ligroin)
Melting point: 100°–102° C.

EXAMPLE 80

4-Methyl-6-[3-(4-benzyl-1-piperidyl)propoxy]carbostyril
Yellowish prism like crystals (from methanol)
Melting point: 177°–178° C.

EXAMPLE 81

4-Methyl-7-[3-(4-benzyl-1-piperidyl)propoxy]carbostyril
Colorless needle-like crystals (from methanol)
Melting point: 183°–184° C.

EXAMPLE 82

8-Bromo-5-[2-hydroxy-3-(4-benzyl-1-piperidyl)propoxy]-3,4-dihydrocarbostyril
Colorless needle-like crystals (from ethanol)
Melting point: 165°–166° C.

EXAMPLE 83

1.8 Grams of 1-methyl-5-hydroxy-3,4-dihydrocarbostyril and 2.3 g of 4-benzyl-1-(2,3-epoxyporpyl)piperidine were mixed with 30 ml of methanol and the mixture was heated under refluxing condition for 3 hours. The reaction mixture was concentrated under a reduced pressure and the residue thus obtained was dissolved in 30 ml of acetone, then 5% oxalic acid-acetone solution was added thereto under stirring at a room temperature to adjust the pH to 4.5 and allowed to stand. Then the precipitates formed were collected by filtration and washed with acetone and recrystallizes from ethanol-ether to obtain 3.5 g (yield: 63%) of 1-methyl-5-[2-hydroxy-3-(4-benzyl-1-piperidyl)propoxy]-3,4-dihydro carbostyril monooxalate as in the form of colorless powdery substance. Melting point: 150°–152° C.

By a method similar to that described in Example 83, there were obtained compounds of Examples 84–94 as follows:

EXAMPLE 84

1-Benzyl-5-[2-hydroxy-3-(4-benzyl-1-piperidyl)propoxy]-3,4-dihydrocarbostyril monooxalate
Colorless powdery substance (from ethanol-ether)
Melting point: 213°–214° C.

EXAMPLE 85

1-Ethyl-5-[2-hydroxy-3-(4-benzyl-1-piperidyl)propoxy]-3,4-dihydrocarbostyril monooxalate
Colorless needle-like crystals (from ethanol)
Melting point: 164°–169° C.

EXAMPLE 86

8-Bromo-5-[2-hydroxy-3-(4-benzyl-1-piperidyl)propoxy]-3,4-dihydrocarbostyril
Colorless needle-like crystals (from ethanol)
Melting point: 165°–166° C.

EXAMPLE 87

5-[2-Hydroxy-3-(4-phenyl-1-piperidyl)propoxy]-3,4-dihydrocarbostyril
Colorless needle-like crystals (from ethanol) Melting point: 207°–208° C.

EXAMPLE 88

6-[2-Hydroxy-3-(4-phenyl-1-piperidyl)propoxy]-3,4-dihydrocarbostyril
Colorless plate-like crystals (from ethanol)
Melting point: 170°–171° C.

EXAMPLE 89

7-[2-Hydroxy-3-(4-phenyl-1-piperidyl)propoxy]-3,4-dihydrocarbostyril
Colorless needle-like crystals (from isopropanol)
Melting point: 149°–150° C.

EXAMPLE 90

1-Allyl-5-[2-hydroxy-3-(4-benzyl-1-piperidyl)propoxy]-3,4-dihydrocarbostyril monooxalate
Colorless needle-like crystals (from ethanol)
Melting point: 178°–180° C.

EXAMPLE 91

1-Allyl-5-[2-hydroxy-3-(4-phenyl-1-piperidyl)propoxy]-3,4-dihydrocarbostyril
Colorless needle-like crystals (from ligroin)
Melting point: 92° C.

EXAMPLE 92

1-Allyl-5-[2-hydroxy-3-(4-phenyl-1-piperidyl)propoxy]-3,4-dihydrocarbostyril monooxalate
Yellowish needle-like crystals (from methanol)
Melting point: 208° C.

EXAMPLE 93

1-Methyl-5-[2-hydroxy-3-(4-benzyl-1-piperidyl)propoxy]-3,4-dihydrocarbostyril monooxalate
Colorless powdery crystals (from ethanol-ether)
Melting point: 150°-152° C.

EXAMPLE 94

5-[2-Hydroxy-3-(3,4,5-trimethoxyphenyl)propoxy]-3,4-dihydrocarbostyril monooxalate
Colorless flake-like crystals (from ethanol)
Melting point: 199°-201° C.

EXAMPLE 95

2.0 Grams of 5-[2-hydroxy-3-(4-phenyl-1-piperidyl)propoxy]-3,4-dihydrocarbostyril and 3 g of methyl iodide were mixed with 30 ml of dimethylformamide and the mixture was stirred at 50°-60° C. for 5 hours. The reaction mixture was concentrated under a reduced pressure and to the residue thus obtained was added 50 ml of acetone and stirred. The precipitates thus formed were collected by filtration and washed with acetone, then recrystallized from methanol-ethanol to obtain 1.7 g of 4-phenyl-1-[2-hydroxy-3-(2-oxo-1,2,3,4-tetrahydroquinolin-5-yloxy)propyl]-1-methylpiperidiniumiodide as in the form of colorless powdery substance. Melting point: 242°-243° C.

By a method similar to that described in Example 95, there were obtained compounds of Examples 96 and 97 as follows:

EXAMPLE 96

4-Phenyl-1-[2-hydroxy-3-(1-allyl-2-oxo-1,2,3,4-tetrahydroquinolin-5-yloxy)propyl]-1-methylpiperidiniumiodide
Colorless needle-like crystals (from isopropanol-acetone)
Melting point: 179°-180° C.

EXAMPLE 97

4-Benzyl-1-[2-hydroxy-3-(1-benzyl-2-oxo-1,2,3,4-tetrahydroquinolin-5-yloxy)propyl]-1-methylpiperidiniumiodide
Yellowish needle-like crystals (from ethanol-ether)
Melting point: 135°-139° C.

EXAMPLE 98

2.0 Grams of 4-phenyl-1-[3-(2-oxo-1,2,3,4-tetrahydroquinolin-7-yloxy)propyl]-1-methylpiperidiniumiodide semihydrate was dissolved in 150 ml of methanol and 100 ml of water, then 3.0 g of silver chloride was added and stirred in a dark and cool place for 24 hours. The reaction mixture was filtered and the mother liquor thus obtained was concentrated under a reduced pressure to dryness. The residue was recrystallized from isopropanol-acetone-ether to obtain 1.0 gram of 4-phenyl-1-[3-(2-oxo-1,2,3,4-tetrahydroquinolin-7-yloxy)propyl]-1-methylpiperidiniumchloride semihydrate as in the form of colorless powdery crystals. Melting point: 211°-213° C.

EXAMPLE 99

2.4 Grams of 7-(3-chloropropoxy)-3,4-dihydrocarbostyril and 4.0 g of 4-hydroxy-4-phenylpiperidine were mixed with 150 ml of toluene and heated under refluxing condition for 24 hours. After cooling the reaction mixture, the precipitates formed were collected by filtration and washed with water, then recrystallized from ethanol. 2.8 Grams of 7-[3-(4-hydroxy-4-phenyl-1-piperidyl)propoxy]-3,4-dihydrocarbostyril was obtained as in the form of colorless flake-like crystals. Melting point: 215° C.

By a method similar to that described in Example 99, there were obtained compounds of Examples 100-107 as follows:

EXAMPLE 100

5-[3-(4-Hydroxy-4-phenyl-1-piperidyl)propoxy]-3,4-dihydrocarbostyril
Colorless needle-like crystals (from methanol)
Melting point: 265°-266° C.

EXAMPLE 101

7-{3-[4-Hydroxy-4-(4-chlorophenyl)-1-piperidyl]propoxy}-3,4-dihydrocarbostyril
Colorless needle-like crystals (from ethanol)
Melting point: 189°-190° C.

EXAMPLE 102

5-[3-(4-Acetyl-4-phenyl-1-piperidyl)propoxy]-3,4-dihydrocarbostyril
Light yellowish prism-like crystals (from ethanol)
Melting point: 165° C.

EXAMPLE 103

7-[3-(4-Acetyl-4-phenyl-1-piperidyl)propoxy]-3,4-dihydrocarbostyril
Colorless needle-like crystals (from isopropanol)
Melting point: 159°-160° C.

EXAMPLE 104

6-[2-(4-Acetyl-4-phenyl-1-piperidyl)ethoxy]-carbostyril
Colorless needle-like crystals (from ethanol)
Melting point: 158°-160° C.

EXAMPLE 105

7-{3-[4-Hydroxy-4-(4-methylphenyl)-1-piperidyl]propoxy}-3,4-dihydrocarbostyril
Colorless flake-like crystals (from ethanol)
Melting point: 188°-189° C.

EXAMPLE 106

7-{3-[4-Hydroxy-4-(2-methoxyphenyl)-1-piperidyl]propoxy}-3,4-dihydrocarbostyril monohydrochloride
Colorless powdery crystals (from methanol-water)
Melting point 239°-241° C.

EXAMPLE 107

4-Methyl-6-{3-[4-(4-acetyl-4-phenyl)-1-piperidyl]propoxy}carbostyril
Light yellowish needle-like crystals (from methanol)
Melting point: 212°-213° C.

EXAMPLE 108

1.43 Grams of 1-methyl-6-(2-bromoethoxy)-3,4-dihydrocarbostyril, 1.3 g of 4-acetyl-4-phenylpiperidine and 1 g of triethylamine were mixed with 30 ml of dimethylformamide and the mixture was heated at 60°-70° C. for 5 hours. The reaction mixture thus obtained was concentrated under a reduced pressure to dryness, and to the residue thus obtained was added 5% sodium hydrogencarbonate aqueous solution and stirred. The insoluble matters were collected by filtration, washed with water then dried and recrystallized from ethanol-water to obtain 1.3 g of 1-methyl-6-[2-(4-acetyl-4-phenyl-1- piperidyl)ethoxy]-3,4-dihydrocarbostyril as in the form of colorless prism-like crystals. Melting point: 101°–103° C.

By a method similar to that described in Example 108, there were obtained compounds of Examples 109–111 as follows:

EXAMPLE 109

1-Methyl-8-[3-(4-acetyl-4-phenyl-1-piperidyl]-propoxy-3,4-dihydrocarbostyril
Colorless needle-like crystals (from ligroin)
Melting point: 103°–105° C.

EXAMPLE 110

1-Methyl-6-[3-(4-acetyl-4-phenyl-1-piperidyl)propoxy]-3,4-dihydrocarbostyril
Colorless needle-like crystals (from ligroin)
Melting point: 115°–117° C.

EXAMPLE 111

4-Methyl-6-{3-[4-(4-acetyl-4-phenyl)-1-piperidyl]-propoxy}-carbostyril
Light yellowish-brown needle-like crystals (from methanol)
Melting point: 212°–213° C.

EXAMPLE 112

1.65 Grams of 6-hydroxycarbostyril and 0.75 g of granular potassium hydroxide were mixed with 50 ml of methanol and concentrated under a reduced pressure to dryness. To the residue obtained was added 50 ml of dimethylformamide and mixed well, then 2.6 g of 1-(3-chloropropyl)-4-acetyl-4-phenylpiperidine was added and heated at 50° C. for 6 hours under stirring condition. The reaction mixture was concentrated under a reduced pressure to dryness and 20 ml of 5%-sodium hydrogencarbonate aqueous solution was added thereto and stirred. The insoluble matters were collected by filtration and washed with water. After dried the insoluble matters were recrystallized from ethanol to obtain 1.1 g of 6-[3-(4-acetyl-4-phenyl-1-piperidyl)propoxy]-carbostyril as in the form of colorless prism-like crystals. Melting point: 192.5°–194° C.

By a method similar to that described in Example 112, there were obtained compounds of Examples 113–123 as follows:

EXAMPLE 113

5-[3-(4-Hydroxy-4-phenyl-1-piperidyl)propoxy]-3,4-dihydrocarbostyril
Colorless needle-like crystals (from methanol)
Melting point: 265°–266° C.

EXAMPLE 114

7-[3-(4-Hydroxy-4-phenyl-1-piperidyl)propoxy]-3,4-dihydrocarbostyril
Colorless flake-like crystals (from ethanol)
Melting point: 215° C.

EXAMPLE 115

7-{3-[4-Hydroxy-4-(4-chlorophenyl)-1-piperidyl]-propoxy}-3,4-dihydrocarbostyril
Colorless needle-like crystals (from ethanol)
Melting point: 189°–190° C.

EXAMPLE 116

5-[3-(4-Acetyl-4-phenyl-1-piperidyl)propoxy]-3,4-dihydrocarbostyril
Light yellowish prism-like crystals (from ethanol)
Melting point: 165° C.

EXAMPLE 117

7-[3-(4-Acetyl-4-phenyl-1-piperidyl)propoxy]-3,4-dihydrocarbostyril
Colorless needle-like crystals (from isopropanol)
Melting point: 159°–160° C.

EXAMPLE 118

6-[2-(4-Acetyl-4-phenyl-1-piperidyl)ethoxy]-3,4-dihydrocarbostyril
Colorless needle-like crystals (from ethanol)
Melting point: 158°–160° C.

EXAMPLE 119

7-{3-[4-Hydroxy-4-(4-methylphenyl)-1-piperidyl]-propoxy}-3,4-dihydrocarbostyril
Colorless flake-like crystals (from ethanol)
Melting point: 188°–189° C.

EXAMPLE 120

7-{3-[4-Hydroxy-4-(2-methoxyphenyl)-1-piperidyl]-propoxy}-3,4-dihydrocarbostyril monohydrochloride
Colorless powdery crystals (from methanol-water)
Melting point: 239°–241° C.

EXAMPLE 121

1-Methyl-6-[2-(4-acetyl-4-phenyl-1-piperidyl)ethoxy]-3,4-dihydrocarbostyril
Colorless prism-like crystals (from ethanol-water)
Melting point: 101°–103° C.

EXAMPLE 122

1-Methyl-8-[3-(4-acetyl-4-phenyl-1-piperidyl)propoxy]-3,4-dihydrocarbostyril
Colorless needle-like crystals (from ligroin)
Melting point: 103°–105° C.

EXAMPLE 123

4-Methyl-6-{3-[4-(4-acetyl-4-phenyl)-1-piperidyl]-propoxy}carbostyril
Light yellowish-brown needle-like crystals (from methanol)
Melting point: 212°–213° C.

EXAMPLE 124

2.0 Grams of 6-[3-(4-acetyl-4-phenyl-1-piperidyl)propoxy]-3,4-dihydrocarbostyril and 0.25 g of sodium hydride (50% in oil) were mixed in 30 ml of dimethylformamide and stirred for 1 hour, then 0.7 g of methyl iodide was added thereto and stirred at a room temperature for 12 hours. The reaction mixture was poured into 80 ml of saturated sodium chloride solution and the organic layer was extracted with chloroform and the chloroform layer was washed with water and dried. Then the chloroform was removed by distillation and the residue was crystallized with hexane. The crude crystals were recrystallized from ligroin to obtain 1.7 g of 1-methyl-6-[3-(4-acetyl-4-phenyl-1-piperidyl)propoxy]-3,4-dihydrocarbostyril as in the form of colorless needle-like crystals. Melting point: 115°–117° C.

By a method similar to that described in Example 124, there were obtained compounds of Examples 125–127 as follows:

EXAMPLE 125

1-Methyl-8-[3-(4-acetyl-4-phenyl-1-piperidyl)propoxy]-3,4-dihydrocarbostyril
Colorless needle-like crystals (from ligroin)
Melting point: 103°–105° C.

EXAMPLE 126

1-Allyl-5-{2-hydroxy-3-[4-(4-acetyl-4-phenyl)-1-piperidyl]propoxy}-3,4-dihydrocarbostyril
Colorless prism-like crystals (from ligroin-benzene)
Melting point: 141°–142° C.

EXAMPLE 127

1-Propargyl-5-{2-hydroxy-3-[4-(4-hydroxy-4-(chlorophenyl)-1-piperidyl]propoxy}-3,4-dihydrocarbostyril
Colorless needle-like crystals (from ligroin-benzene-acetone)
Melting point: 132°–134° C.

EXAMPLE 128

2.9 Grams of 1-allyl-5-(2,3-epoxypropoxy)-3,4-dihydrocarbostyril and 2.3 g of 4-acetyl-4-phenylpiperidine were mixed with 30 ml of methanol and the mixture was heated under refluxing condition for 3 hours. The reaction mixture was concentrated under a reduced pressure and the residue obtained was dissolved in 30 ml of acetone, then under stirring at a room temperature 5%-oxalic acid-acetone solution was added to adjust the pH to 4.5, and allowed to stand. The precipitates formed were collected by filtration, and washed with acetone. Recrystallized from ligroin-benzene to obtain 2.72 g of 1-allyl-5-{2-hydroxy-3-[4-(4-acetyl-4-phenyl)-1-piperidyl]propoxy}-3,4-dihydrocarbostyril as in the form of colorless prism-like crystals. Melting point: 141°–142° C.

By a method similar to that described in Example 128, there were obtained compounds of Examples 129–130 as follows:

EXAMPLE 129

1-Propargyl-5-{2-hydroxy-3-[4-(4-hydroxy-4-(2-chlorophenyl)-1-piperidyl]propoxy}-3,4-dihydrocarbostyril
Colorless needle-like crystals (from ligroin-benzene-acetone)
Melting point: 132°–134° C.

EXAMPLE 130

4-Phenyl-6-{2-hydroxy-3-[4-(4-hydroxy-4-phenyl)]-1-piperidyl}propoxy-3,4-dihydrocarbostyril
Colorless prism-like crystals (from ethanol-water)
Melting point: 177°–178° C.

EXAMPLE 131

1.8 Grams of 1-allyl-5-hydroxy-3,4-dihydrocarbostyril and 2.6 g of 4-acetyl-4-phenyl-1-(2,3-epoxypropyl)-piperidine were mixed in 30 ml of methanol and the mixture was heated under refluxing condition for 3 hours. The reaction mixture was concentrated under a reduced pressure and the residue obtained was dissolved in 30 ml of acetone. Then under stirring at a room temperature, 5%-oxalic acid-acetone solution was added to adjust the pH to 4.5 and allowed to stand. The precipitates formed were collected by filtration and washed with acetone then recrystallized from ligroin-benzene to obtain 2.62 g of 1-allyl-5-{2-hydroxy-3-[4-(4-acetyl-4-phenyl)-1-piperidyl]propoxy}-3,4-dihydrocarbostyril as in the form of colorless powdery substance.
Melting point: 141°–142° C.

By a method similar to that described in Example 131, there were obtained compounds of Examples 132–133 as follows:

EXAMPLE 132

1-Propargyl-5-{2-hydroxy-3- 4-[4-hydroxy-4-(2-chlorophenyl)]-1-piperidyl propoxy}-3,4-dihydrocarbostyril
Colorless needle-like crystals (from ligroinbenzene-acetone)
Melting point: 132°–134° C.

EXAMPLE 133

4-Phenyl-6-{2-hydroxy-3-[4-(4-hydroxy-4-phenyl)-piperidyl]propoxy}-3,4-dihydrocarbostyril
Colorless prism-like crystals (from ethanol-water)
Melting point: 177°–178° C.

What is claimed is:

1. A carbostyril derivative or a pharmaceutically acceptable salt thereof, said carbostyril derivative being represented by the general formula (1),

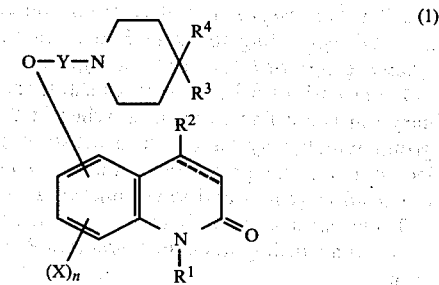

wherein $R^1$ is a hydrogen atom, a lower alkenyl group, a lower alkynyl group or a lower alkyl group which may have phenyl group(s) as the substituted group(s); $R^2$ is a hydrogen atom, a lower alkyl group or a phenyl group; $R^3$ is a lower alkyl group having phenyl group(s) as the substituted group(s), or a phenyl group which may have 1 to 3 substituted groups selected from the group consisting of halogen atoms, lower alkyl groups and lower alkoxy groups; $R^4$ is a hydrogen atom, a hydroxyl group or a lower alkanoyl group; X is a halogen atom; Y is a lower alkylene group which may have hydroxyl group(s) as the substituent(s); n is 0, 1 or 2; the carbon-carbon bond between 3- and 4-positions in the carbostyril skeleton is a single or double bond; provided that when $R^3$ is a lower alkyl group having phenyl group(s) as the substituted group(s) then $R^4$ should be neither a hydroxyl group nor a lower alkanoyl group, or a quaternary salt represented by the general formula (1e),

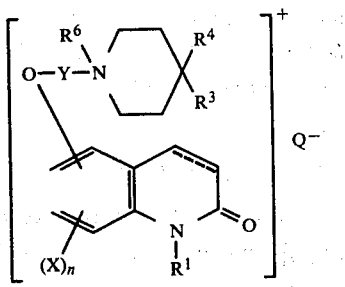

wherein $R^1$, $R^2$, $R^3$, $R^4$, Y, n and the carbon-carbon bond between 3- and 4-positions in the carbostyril skeleton are the same as defined above, $R^6$ is a lower alkyl group and Q is a halogen atom.

2. The carbostyril derivative or salt thereof or quaternary salt according to claim 1, wherein $R^4$ is a hydrogen atom.

3. The carbostyril derivative or salt thereof or quaternary salt according to claim 2, wherein $R^3$ is a phenyl group or a lower alkyl group having phenyl group(s) as the substituted group(s).

4. The carbostyril derivative or salt thereof or quaternary salt according to claim 3, wherein $R^1$ is a hydrogen atom.

5. The carbostyril derivative or salt thereof or quaternary salt according to claim 3, wherein $R^1$ is a lower alkyl group which may have phenyl group(s) as the substituted group(s).

6. The carbostyril derivative or salt thereof or quaternary salt according to claim 3, wherein $R^1$ is a lower alkenyl group or a lower alkynyl group.

7. The carbostyril derivative or salt thereof or quaternary salt according to claim 2, wherein $R^3$ is a phenyl group which may have 1 to 3 substituted groups selected from the group consisting of halogen atoms, lower alkyl groups and lower alkoxy groups.

8. The carbostyril derivative or salt thereof or quaternary salt according to claim 7, wherein $R^1$ is a hydrogen atom.

9. The carbostyril derivative or salt thereof or quaternary salt according to claim 7, wherein $R^1$ is a lower alkyl group which may have phenyl group(s) as the substituted group(s).

10. The carbostyril derivative or salt thereof or quaternary salt according to claim 7, wherein $R^1$ is a lower alkenyl group or a lower alkynyl group.

11. The carbostyril derivative or salt thereof or quaternary salt according to claim 1, wherein $R^4$ is a hydroxyl group or a lower alkanoyl group.

12. The carbostyril derivative or salt thereof or quaternary salt according to claim 11, wherein $R^1$ is a hydrogen atom.

13. The carbostyril derivative or salt thereof or quaternary salt according to claim 11, wherein $R^1$ is a lower alkyl group which may have phenyl group(s) as the substituted group(s).

14. The carbostyril derivative or salt thereof or quaternary salt according to claim 11, wherein $R^1$ is a lower alkenyl group or a lower alkynyl group.

15. The carbostyril derivative or salt thereof or quaternary salt according to claim 3, claim 7 or claim 11, wherein Y is a lower alkylene group.

16. The carbostyril derivative or salt thereof or quaternary salt according to claim 3, claim 7 or claim 11, wherein Y is a lower alkylene group having hydroxyl group(s) as the substituted group(s).

17. 1-Methyl-5-[3-(4-benzyl-1-piperidyl)propoxy]-3,4-dihydrocarbostyril.

18. 7-[3-(4-Benzyl-1-piperidyl)propoxy]-3,4-dihydrocarbostyril.

19. 7-[3-(4-Phenyl-1-piperidyl)propoxy]-3,4-dihydrocarbostyril.

20. 1-Benzyl-5-[2-hydroxy-3-(4-benzyl-1-piperidyl)propoxy]-3,4-dihydrocarbostyril.

21. 1-Ethyl-5-[2-hydroxy-3-(4-benzyl-1-piperidyl)propoxy]-3,4-dihydrocarbostyril.

22. 7-[2-Hydroxy-3-(4-phenyl-1-piperidyl)propoxy]-3,4-dihydrocarbostyril.

23. 1-(3-Phenylpropyl)-7-[3-(4-phenyl-1-piperidyl)propoxy]-3,4-dihydrocarbostyril.

24. An antihistaminic agent containing an antihistaminically effective amount of at least one carbostyril derivative or pharmaceutically acceptable salt thereof or quaternary salt of claim 1 as the active ingredient.

* * * * *